United States Patent
Richter et al.

(10) Patent No.: US 12,161,658 B2
(45) Date of Patent: Dec. 10, 2024

(54) COMPOSITIONS AND METHODS FOR THE TREATMENT OF EXPANDED REPEAT-ASSOCIATED DISORDERS

(71) Applicant: UNIVERSITY OF MASSACHUSETTS, Boston, MA (US)

(72) Inventors: Joel D. Richter, Boston, MA (US); Fen-Biao Gao, Boston, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 733 days.

(21) Appl. No.: 17/130,908

(22) Filed: Dec. 22, 2020

(65) Prior Publication Data

US 2021/0236534 A1 Aug. 5, 2021

Related U.S. Application Data

(63) Continuation of application No. 16/185,543, filed on Nov. 9, 2018, now Pat. No. 10,905,707.

(60) Provisional application No. 62/584,176, filed on Nov. 10, 2017.

(51) Int. Cl.
| | | |
|---|---|---|
| A61K 31/7105 | (2006.01) | |
| A61K 31/7088 | (2006.01) | |
| A61K 31/711 | (2006.01) | |
| A61K 31/7115 | (2006.01) | |
| A61K 31/712 | (2006.01) | |
| A61P 25/28 | (2006.01) | |
| C12N 9/22 | (2006.01) | |
| C12N 15/113 | (2010.01) | |

(52) U.S. Cl.
CPC ...... *A61K 31/7105* (2013.01); *A61K 31/7088* (2013.01); *A61K 31/711* (2013.01); *A61K 31/7115* (2013.01); *A61K 31/712* (2013.01); *A61P 25/28* (2018.01); *C12N 9/22* (2013.01); *C12N 15/113* (2013.01); *C12N 2310/314* (2013.01); *C12N 2310/321* (2013.01); *C12N 2310/322* (2013.01); *C12N 2310/3233* (2013.01)

(58) Field of Classification Search
CPC .............. A61K 31/7088; A61K 31/712; A61K 31/7115; A61P 25/28; C12N 9/22; C12N 15/113; C12N 2310/314; C12N 2310/321; C12N 2310/322
USPC .............. 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 10,905,707 B2 * | 2/2021 | Richter | C12N 15/113 |
| 2015/0259679 A1 | 9/2015 | Bennett et al. | |
| 2015/0267197 A1 | 9/2015 | Bennett et al. | |
| 2016/0024496 A1 | 1/2016 | Bennett et al. | |
| 2016/0230172 A1 | 8/2016 | Rigo et al. | |
| 2016/0237432 A1 | 8/2016 | Bennett et al. | |
| 2016/0251655 A1 | 9/2016 | Freier et al. | |
| 2016/0304871 A1 | 10/2016 | Rigo et al. | |

FOREIGN PATENT DOCUMENTS

| | | | | |
|---|---|---|---|---|
| WO | WO-2015054676 A2 * | 4/2015 | ........... | A61K 31/711 |
| WO | WO 2016/112132 A1 | 7/2016 | | |
| WO | WO 2016/167780 A1 | 10/2016 | | |
| WO | WO 2017/079291 A1 | 5/2017 | | |
| WO | WO-2017109757 A1 * | 6/2017 | ........... | A61K 31/395 |
| WO | WO 2017/180835 A1 | 10/2017 | | |

OTHER PUBLICATIONS

U.S. Appl. No. 16/185,543, filed Nov. 9, 2018, 2019/0231808, Aug. 1, 2019, U.S. Pat. No. 10,905,707, Joel D. Richter.
U.S. Appl. No. 17/130,908, filed Dec. 22, 2020, 2021/0236534, Aug. 5, 2021, Joel D. Richter.
Ash et al. (2013) "Unconventional Translation of C9ORF72 GGGGCC Expansion Generates Insoluble Polypetides Specific to c9FTD/ALS," Neuron, 77:639-646.
Cheng et al. (2018) "C9ORF72 GGGGCC repeat-associated non-AUG translation is upregulated by stress through eIF2a phosphorylation," Nature Communications, 9(51):12 pages.
Dejesus-Hernandez et al. (2011) "Expanded GGGGCC Hexanucleotide Repeat in Noncoding Region of C9ORF72 Causes Chromosome 9p-Linked FTD and ALS," Neuron, 72:245-256.
Freibaum et al. (2017) "The Role of Dipeptide Repeats in C9ORF72-Related ALS-FTD," Frontiers in Molecular Neuroscience, 10(35):9 pages.
Ingolia et al. (2009) "Genome-Wide Analysis in Vivo of Translation with Nucleotide Resolution Using Ribosome Profiling," Science, 324:218-223.
Ingolia et al. (2011) "Ribosome Profiling of Mouse Embryonic Stem Cells Reveals the Complexity and Dynamics of Mammalian Proteomes," Cell, 147:789-802.
International Search Report and Written Opinion for International Application No. PCT/US18/59985, dated Apr. 12, 2019.
Jiang et al. "Gain of Toxicity from ALS/FTD-Linked Repeat Expansions in C9ORF72 Is Alleviated by Antisense Oligonucleotides Targeting GGGGCC-Containing RNAs," Neuron, 90:535-550.
Lee et al. (2012) "Global mapping of translation initiation sites in mammalian cells at single-nucleotide resolution," PNAS, E2424-E2432.
Liu et al. (2016) C9orf72 BAC Mouse Model with Motor Deficits and Neurodegenerative Features of ALS/FTD, Neuro, 90:521-534.

(Continued)

*Primary Examiner* — Jane J Zara
(74) *Attorney, Agent, or Firm* — LATHROP GPM LLP; James H. Velema, Esq.; Michael J. Spellberg, Esq.

(57) ABSTRACT

Translation modulating agents that modulate expression of one or more translation start sites for expanded repeat (e.g., DPR) protein synthesis are provided. Compositions and methods for treating translation start sites for expanded repeat (e.g., DPR) protein synthesis-associated disorders are also provided.

12 Claims, 13 Drawing Sheets

Specification includes a Sequence Listing.

(56) References Cited

OTHER PUBLICATIONS

Lopez-Gonzalez et al. (2016) "Poly(GR) in C9ORF72-Related ALS/FTD Compromises Mitochondrial Function and Increases Oxidative Stress and DNA Damage in iPSC-Derived Motor Neurons," Neuron, 92:383-391.

Mori et al. (2013) "The C9orf72 GGGGCC Repeat Is Translated into Aggregating Dipeptide-Repeat Proteins in FTLD/ALS," Science Express, 6 pages.

O'Rourke et al. (2015) "C9orf72 BAC Transgenic Mice Display Typical Pathologic Features of ALS/FTD," Neuron, 88:892-901.

Peters et al. (2015) "Human C9ORF72 Hexanucleotide Expansion Reproduces RNA Foci and Dipeptide Repeat Proteins but Not Neurodegeneration in BAC Transgenic Mice," Neuron, 88:902-909.

Renton et al. (2011) "A Hexanucleotide Repeat Expansion in C9ORF72 Is the Cause of Chromosome 9p21-Linked ALS-FTD," Neuron, 72:257-268.

Tran et al. (2015) "Differential Toxicity of Nuclear RNA Foci versus Dipeptide Repeat Proteins in a Drosophila Model of C9ORF72 FTD/ALS," Neuron, 87:1207-1214.

Wojciechowska et al. (2014) "RAN translation and framshifting as translational challenges at simple repeats of human neurodegenerative disorders," Nucleic Acids Research, 42(19):11849-11864.

\* cited by examiner

RNA Derived from GGGGCC C9ORF72 Expanded Repeats Form aggregates in Nuclei

Peptide Aggregates Derived from GGGGCC C9ORF72 Expanded Repeat

SEQUENCE LISTING

<160> NUMBER OF SEQ ID NOS: 20

<210> SEQ ID NO 1
<211> LENGTH: 185
<212> TYPE: DNA
<213> ORGANISM: Unknown
<220> FEATURE:
<223> OTHER INFORMATION: Description of Unknown:
      C9ORF72 sequence

<400> SEQUENCE: 1
gtgtgtgttt tgtttttcc caccctctct ccccactact tgctctcaca gtactcgctg     60
agggtgaaca agaaaagacc tgataaagat taaccagaag aaaacaagga gggaaacaac    120
cgcagcctgt agcaagctct ggaactcagg agtcgcgcgc tagggccgg ggccggggcc    180 ggggc                                                                185

<210> SEQ ID NO 2
<211> LENGTH: 22
<212> TYPE: DNA
<213> ORGANISM: Unknown
<220> FEATURE:
<223> OTHER INFORMATION: Description of Unknown:
      C9ORF72 sequence

<400> SEQUENCE: 2
acctgataaa gattaaccag aa                                              22

<210> SEQ ID NO 3
<211> LENGTH: 22
<212> TYPE: DNA
<213> ORGANISM: Unknown
<220> FEATURE:
<223> OTHER INFORMATION: Description of Unknown:
      C9ORF72 sequence

<400> SEQUENCE: 3
tgtagcaagc tctggaactc ag                                              22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctctcacag tactcgctga                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgtagcaagc tctggaactc                                                 20

<210> SEQ ID NO 6
<211> LENGTH: 86
<212> TYPE: DNA
<213> ORGANISM: Unknown
<220> FEATURE:

-continued

```
<223> OTHER INFORMATION: Description of Unknown:
      C9ORF72 sequence

<400> SEQUENCE: 6
tgagggtgaa caagaaaaga cctgataaag attaaccaga agaaaacaag gagggaaaca      60
accgcagcct gtagcaagct ctggaa                                          86

<210> SEQ ID NO 7
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Arg Gly Arg Gly Arg Gly Arg Gly Arg Gly Arg Gly Arg Gly Arg
1               5                   10                  15

Gly Arg Gly Arg Gly Arg Gly Arg Gly Arg Gly Arg Gly Arg Gly Arg
            20                  25                  30

Gly Arg Gly Arg Gly Arg Gly Arg Gly Arg Gly Arg Gly Arg Gly Arg
        35                  40                  45

Gly Arg Gly Arg Gly Arg Gly Arg Gly Arg Gly Arg Gly Arg Gly Arg
    50                  55                  60

Gly Arg Gly Arg Gly Arg Gly Arg Gly Arg Gly Arg Gly Arg Gly Arg
65                  70                  75                  80

Gly Arg Gly Arg Gly Arg Gly Arg Gly Arg Gly Arg Gly Arg Gly Arg
                85                  90                  95

Gly Arg Gly Arg Gly Arg Gly Arg Gly Arg Gly Arg Gly Arg Gly Arg
            100                 105                 110

Gly Arg Gly Arg Gly Arg Gly Arg Gly Arg Gly Arg Gly Arg Gly Arg
        115                 120                 125

Gly Arg Gly Arg Gly Arg Gly Arg Gly Arg Gly Arg Gly Arg Gly Arg
    130                 135                 140

Gly Arg Gly Arg Gly Arg Gly Arg Gly Arg Gly Arg Gly Arg Gly Arg
145                 150                 155                 160

<210> SEQ ID NO 8
<211> LENGTH: 18
<212> TYPE: RNA
<213> ORGANISM: Unknown
<220> FEATURE:
<223> OTHER INFORMATION: Description of Unknown:
      C9ORF72 sequence

<400> SEQUENCE: 8
ggggccgggg ccggggcc                                                   18

<210> SEQ ID NO 9
<211> LENGTH: 18
<212> TYPE: RNA
<213> ORGANISM: Unknown
<220> FEATURE:
<223> OTHER INFORMATION: Description of Unknown:
      C9ORF72 sequence

<400> SEQUENCE: 9
ggccccggcc ccggcccc                                                   18

<210> SEQ ID NO 10
<211> LENGTH: 180
```

<212> TYPE: DNA
<213> ORGANISM: Unknown
<220> FEATURE:
<223> OTHER INFORMATION: Description of Unknown:
      C9ORF72 sequence

<400> SEQUENCE: 10
gtgtgtgttt tgtttttcc caccctctct ccccactact tgctctcaca gtactcgctg      60
agggtgaaca agaaaagacc tgataaagat taaccagaag aaaacaagga gggaaacaac    120
cgcagcctgt agcaagctct ggaactcagg agtcgcgcgc taggggccgg ggccggggcc    180

<210> SEQ ID NO 11
<211> LENGTH: 450
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ggggccgggg ccggggccgg ggccggggcc ggggccgggg ccggggccgg ggccggggcc     60
ggggccgggg ccggggccgg ggccggggcc ggggccgggg ccggggccgg ggccggggcc    120
ggggccgggg ccggggccgg ggccggggcc ggggccgggg ccggggccgg ggccggggcc    180
ggggccgggg ccggggccgg ggccggggcc ggggccgggg ccggggccgg ggccggggcc    240
ggggccgggg ccggggccgg ggccggggcc ggggccgggg ccggggccgg ggccggggcc    300
ggggccgggg ccggggccgg ggccggggcc ggggccgggg ccggggccgg ggccggggcc    360
ggggccgggg ccggggccgg ggccggggcc ggggccgggg ccggggccgg ggccggggcc    420
ggggccgggg ccggggccgg ggccggggcc                                    450

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Gly Leu Arg Leu
1               5

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Gly Pro Gly Pro Gly Arg Gly Arg Gly Gly Pro Gly Gly Gly Pro
1               5                   10                  15

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Thr Arg Lys Asp Leu Ile Lys Ile Asn Gln Lys Lys Thr Arg Arg Glu
1               5                   10                  15

Thr Thr Ala Ala Cys Ser Lys Leu Trp Asn Ser Gly Val Ala Arg
            20                  25                  30
```

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Cys Val Phe Leu Phe Phe Pro Pro Ser Leu Pro Thr Thr Cys Ser His
1               5                   10                  15

Ser Thr Arg
```

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gln Ala Leu Glu Leu Arg Ser Arg Ala Leu Gly Ala Gly Ala Gly Ala
1               5                   10                  15

Gly Ala Trp Ser Gly Arg Ala Arg Gly Arg Ala Arg Gly Gly Ala Ala
            20                  25                  30

Val
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Pro Glu Glu Asn Lys Glu Gly Asn Asn Arg Ser Leu
1               5                   10
```

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Val Cys Val Phe Val Phe Pro Thr Leu Ser Pro His Tyr Leu Leu Ser
1               5                   10                  15

Gln Tyr Ser Leu Arg Val Asn Lys Lys Arg Pro Asp Lys Asp
            20                  25                  30
```

<210> SEQ ID NO 19
<211> LENGTH: 48
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 19

Arg Leu Thr Arg Arg Lys Gln Gly Gly Lys Gln Pro Gln Pro Val Ala
1               5                   10                  15

Ser Ser Gly Thr Gln Glu Ser Arg Ala Arg Gly Arg Gly Arg Gly Arg
                20                  25                  30

Gly Val Val Gly Ala Gly Pro Gly Ala Gly Pro Gly Arg Gly Cys Gly
            35                  40                  45

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Cys Phe Cys Phe Ser His Pro Leu Ser Pro Leu Leu Ala Leu Thr
1               5                   10                  15

Val Leu Ala Glu Gly Glu Gln Glu Lys Thr
                20                  25
```

COMPOSITIONS AND METHODS FOR THE TREATMENT OF EXPANDED REPEAT-ASSOCIATED DISORDERS

RELATED APPLICATIONS

This application is a continuation of U.S. patent application Ser. No. 16/185,543, filed Nov. 9, 2018, which claims priority to U.S. Provisional Patent Application Ser. No. 62/584,176, filed Nov. 10, 2017, the contents of which are incorporated by reference herein for all purposes.

STATEMENT OF FEDERALLY SPONSORED RESEARCH

This invention was made with government support under Grant numbers NS101986 and NS109847 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Dec. 21, 2020, is named 711584_UM9-225CON_ST25.txt and is 8,219 bytes in size.

FIELD OF THE INVENTION

This disclosure relates to compositions and methods for treating expanded repeat-associated disorders (e.g., amyotrophic lateral sclerosis, frontotemporal dementia and the like).

BACKGROUND

Repeat expansion regions in mRNA transcripts and the genes that encode them are associated with numerous neurological diseases. Examples of such repeats and the diseases they are associated with include the CGG repeat in the FMR1 gene, the ATTCT repeat in the ATXN10 gene, the CCTG repeat in the ZNF9 gene, the GGGGCC repeat in the C9ORF72 gene, the CAG repeat in the ATXN3 and HTT genes, and the CTG repeat in the DMPK, JPH3, and ATXN8OS genes. These repeat expansion regions in the transcripts may lead to mRNA and protein aggregation which is believed to play a role in the pathogenesis of several neurological diseases. Additionally, the repeat regions of the mRNA have been thought to lead to the production of toxic dipeptide repeat (DPR) proteins in C9ORF72-related ALS/FTD; however, the initiation sites for DPR protein synthesis are mostly unknown.

The GGGGCC (G4C2) repeat expansion in a noncoding region of C9ORF72 is the most common cause of sporadic and familial forms of amyotrophic lateral sclerosis (ALS) and frontotemporal dementia (FTD) (DeJesus-Hernandez M, et al. Neuron. 2011; 72:245-256; Renton A E, et al. Neuron. 2011; 72:257-268). Repeat-associated degeneration in neuronal tissues and DPR proteins are observed in patients as a potential cause of the pathogenesis of these diseases (Ash et al., Neuron 2013; 77:639-646; Mon et al., Science 2013; 339: 1335-1338).

Ectopic expression of expanded G4C2 repeats flanked by human introns results in the formation of nuclear RNA foci and production of DPR proteins through unknown mechanisms without causing gross neurodegeneration in flies or some mouse models (Tran et al., 2015; O'Rourke et al., 2015; Peters et al., 2015; Jiang et al., 2016), although some behavioral phenotypes were observed when expanded G4C2 repeats were expressed at higher levels or in a different genetic background (Jiang et al., 2016; Liu et al., 2016).

Among the C9ORF72 DPR proteins expressed from the GGGGCC repeat, ectopic expression of the DPR protein (GR)80 (SEQ ID NO: 7) in iPSC-derived control neurons increased DNA damage, suggesting poly(GR) contributes to DNA damage in aged C9ORF72 neurons (Lopez-Gonzalez et al. Neuron. 2016 92:383-391).

ALS occurs in both familial (fALS) and sporadic (sALS) forms. A significant number of fALS cases are associated with expansions of a non-coding hexanucleotide GGGGCC expansion in the gene C9ORF72. These expansions are also detected in 10-20% of familial frontotemporal dementia (FTD), 10% of sporadic FTD (sFTD) and in about 5% of sALS. These statistics define the C9ORF72 GGGGCC expansion as a common cause of ALS and FTD. In normal individuals, the GGGGCC expansion ranges in size from 2 or 3 to upwards of 25 repeats; by contrast, FTD/ALS patients have hundreds or even thousands of these repeats. Transcription from the normal C9ORF72 gene yields three mRNA variants V1 (e.g., GenBank: NM_145005.6), V2 (e.g., GenBank: NM_018325.3), and V3 (e.g., GenBank: NM_001256054.1). Transcript V1 contains exons 1a-6b and codes for a 222 amino acid protein. Exons V2 and V3 respectively contain exons 2-12 and exons 1b-12 and code for the same 481 amino acid protein.

The ability to identify, target, and inhibit one or more translation start sites for expanded repeat (e.g., DPR) protein synthesis would provide a potential therapeutic avenue to treat or prevent diseases or disorders associated with these repeat regions, such as ALS and FTD.

SUMMARY

The present disclosure in based in part on the discovery that certain translation start sites for expanded repeat (e.g., DPR) protein synthesis are associated with diseases and/or disorders associated with repeat expansion regions. The present disclosure is also based on the discovery of novel translation start sites for expanded repeat (e.g., DPR) protein synthesis in C9ORF72 mRNAs having a GGGGCC repeat expansion in human cells. The novel start sites described herein mediate translation of toxic dipeptide repeat (e.g., DPR)-containing proteins that can form aggregations associated with a variety of diseases such as, e.g., amyotrophic lateral sclerosis (ALS) and frontotemporal dementia (FTD).

In one aspect, a translation modulating agent comprising a nucleic acid sequence that is sufficiently complementary to a region at or near a translation start site for expanded repeat (e.g., DPR) protein synthesis of an mRNA to modulate expression of the mRNA is provided.

In certain exemplary embodiments, the agent is a nucleic acid sequence selected from the group consisting of an ASO, a small interfering RNA (siRNA), and a guide RNA.

In certain exemplary embodiments, the guide RNA comprises SEQ ID NO: 4 and/or SEQ ID NO: 5.

In certain exemplary embodiments, the guide RNAs of SEQ ID NO: 4 and SEQ ID NO: 5 flank the C9ORF72 gene region of SEQ ID NO: 6.

In certain exemplary embodiments, a translation start site for expanded repeat (e.g., DPR) protein synthesis is at or near a repeat expansion region selected from the group consisting of CAG, CGG, and GGGGCC. The repeat expansion region may optionally be associated with a disease or disorder selected from the group consisting of spinocerebellar ataxia type 3, spinocerebellar ataxia type 8, myotonic dystrophy type 1, fragile X tremor/ataxia syndrome, amyotrophic lateral sclerosis, frontotemporal dementia, and Huntington's disease. The agent may optionally be a nucleic acid sequence that is sufficiently complementary to an mRNA or a gene region within 100 bases of the 5' end of the repeat expansion region to modulate expression of the mRNA, wherein the agent is a polypeptide that binds to an mRNA or a gene region within 100 bases of the 5' end of the repeat expansion region.

In certain exemplary embodiments, the agent disrupts a translation start site for expanded repeat (e.g., DPR) protein synthesis encoded by intron 1 of a C9ORF72 gene or a C9ORF72 mRNA to inhibit C9ORF72 expression. The translation start site for expanded repeat (e.g., DPR) protein synthesis can optionally be upstream of a GGGGCC repeat expansion region in the C9ORF72 gene or the C9ORF72 mRNA. The agent is optionally sufficiently complementary to a region comprising SEQ ID NO: 1 to disrupt a translation initiation start codon. The agent is optionally sufficiently complementary to a region comprising SEQ ID NO: 2 or SEQ ID NO: 3 to disrupt a translation initiation start codon.

In certain exemplary embodiments, the agent comprises an antisense oligonucleotide (ASO). The ASO is optionally sufficiently complementary to a C9ORF72 mRNA to disrupt translation initiation at a translation start site for expanded repeat (e.g., DPR) protein synthesis of the C9ORF72 mRNA. The ASO optionally comprises one or more modifications, e.g., one or more modifications are selected from the group consisting of a 2'-O-methyl modified nucleotide, a 2'-fluoro modified nucleotide, a nucleotide comprising a 5'-phosphorothioate group, a terminal nucleotide linked to a cholesterol derivative or hydrophobic molecule, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, a morpholino nucleotide, a phosphoramidate, and a non-natural base comprising nucleotide. The ASO is optionally between about 5 to about 100 nucleotides in length or between about 10 to about 50 nucleotides in length.

In certain exemplary embodiments, the C9ORF72 mRNA is C9ORF72 variant 3, designated as NM_001256054.2.

In certain exemplary embodiments, the agent prevents ribosome binding to the C9ORF72 mRNA.

In certain exemplary embodiments, the agent inhibits translation of a C9ORF72 GGGGCC repeat expansion.

In another aspect, a translation modulating agent comprising a nucleic acid sequence that is sufficiently complementary to a gene at or near a translation start site for expanded repeat (e.g., DPR) protein synthesis encoded by the gene to modulate expression of the gene is provided.

In certain exemplary embodiments, the agent is a nucleic acid sequence selected from the group consisting of an antisense oligonucleotide, a small interfering RNA (siRNA), and a guide RNA.

In certain exemplary embodiments, a translation start site for expanded repeat (e.g., DPR) protein synthesis is at or near a repeat expansion region selected from the group consisting of CAG, CGG, and GGGGCC. The repeat expansion region may optionally be associated with a disease or disorder selected from the group consisting of spinocerebellar ataxia type 3, spinocerebellar ataxia type 8, myotonic dystrophy type 1, fragile X tremor/ataxia syndrome, amyotrophic lateral sclerosis, frontotemporal dementia, and Huntington's disease. The agent may optionally be a nucleic acid sequence that is sufficiently complementary to an mRNA or a gene region within 100 bases of the 5' end of the repeat expansion region to modulate expression of the mRNA, wherein the agent is a polypeptide that binds to an mRNA or a gene region within 100 bases of the 5' end of the repeat expansion region.

In certain exemplary embodiments, the agent disrupts a translation start site for expanded repeat (e.g., DPR) protein synthesis encoded by intron 1 of a C9ORF72 gene or a C9ORF72 mRNA to inhibit C9ORF72 expression. A translation start site for expanded repeat (e.g., DPR) protein synthesis can optionally be upstream of a GGGGCC repeat expansion region in the C9ORF72 gene or the C9ORF72 mRNA. The agent is optionally sufficiently complementary to a region comprising SEQ ID NO: 1 to disrupt a translation initiation start codon. The agent is optionally sufficiently complementary to a region comprising SEQ ID NO: 2 or SEQ ID NO: 3 to disrupt a translation initiation start codon.

In certain exemplary embodiments, the agent comprises an antisense oligonucleotide. The antisense oligonucleotide is optionally sufficiently complementary to a C9ORF72 mRNA to disrupt translation initiation at a translation start site for expanded repeat (e.g., DPR) protein synthesis of the C9ORF72 mRNA. The antisense oligonucleotide optionally comprises one or more modifications, e.g., one or more modifications are selected from the group consisting of a 2'-O-methyl modified nucleotide, a 2'-fluoro modified nucleotide, a nucleotide comprising a 5'-phosphorothioate group, a terminal nucleotide linked to a cholesterol derivative or hydrophobic molecule, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, a morpholino nucleotide, a phosphoramidate, and a non-natural base comprising nucleotide. The antisense oligonucleotide is optionally between about 5 to about 100 nucleotides in length or between about 10 to about 50 nucleotides in length.

In certain exemplary embodiments, the C9ORF72 mRNA is C9ORF72 variant 3, designated as NM_001256054.2.

In certain exemplary embodiments, the agent prevents ribosome binding to the C9ORF72 mRNA.

In certain exemplary embodiments, the agent inhibits translation of a C9ORF72 GGGGCC repeat expansion.

In another aspect, a translation modulating agent comprising a polypeptide that binds an mRNA at or near a translation start site for expanded repeat (e.g., DPR) protein synthesis to modulate expression of the mRNA is provided.

In certain exemplary embodiments, the agent is a polypeptide selected from the group consisting of a zinc finger nuclease (ZFN), a transcription-activator like effector nuclease (TALEN), and an RNA-guided nuclease.

In certain exemplary embodiments, a translation start site for expanded repeat (e.g., DPR) protein synthesis is at or near a repeat expansion region selected from the group consisting of CAG, CGG, and GGGGCC. The repeat expansion region may optionally be associated with a disease or disorder selected from the group consisting of spinocerebellar ataxia type 3, spinocerebellar ataxia type 8, myotonic dystrophy type 1, fragile X tremor/ataxia syndrome, amyotrophic lateral sclerosis, frontotemporal dementia, and Huntington's disease. The agent may optionally be a nucleic acid sequence that is sufficiently complementary to an mRNA or a gene region within 100 bases of the 5' end of the repeat expansion region to modulate expression of the mRNA, wherein the agent is a polypeptide that binds to an mRNA or a gene region within 100 bases of the 5' end of the repeat expansion region.

In certain exemplary embodiments, the agent disrupts a translation start site for expanded repeat (e.g., DPR) protein synthesis encoded by intron 1 of a C9ORF72 gene or a C9ORF72 mRNA to inhibit C9ORF72 expression. A translation start site for expanded repeat (e.g., DPR) protein synthesis can optionally be upstream of a GGGGCC repeat expansion region in the C9ORF72 gene or the C9ORF72 mRNA. The agent is optionally sufficiently complementary to a region comprising SEQ ID NO: 1 to disrupt a translation initiation start codon. The agent is optionally sufficiently complementary to a region comprising SEQ ID NO: 2 or SEQ ID NO: 3 to disrupt a translation initiation start codon.

In certain exemplary embodiments, the agent comprises an antisense oligonucleotide. The antisense oligonucleotide is optionally sufficiently complementary to a C9ORF72 mRNA to disrupt translation initiation at a translation start site for expanded repeat (e.g., DPR) protein synthesis of the C9ORF72 mRNA. The antisense oligonucleotide optionally comprises one or more modifications, e.g., one or more modifications are selected from the group consisting of a 2'-O-methyl modified nucleotide, a 2'-fluoro modified nucleotide, a nucleotide comprising a 5'-phosphorothioate group, a terminal nucleotide linked to a cholesterol derivative or hydrophobic molecule, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, a morpholino nucleotide, a phosphoramidate, and a non-natural base comprising nucleotide. The antisense oligonucleotide is optionally between about 5 to about 100 nucleotides in length or between about 10 to about 50 nucleotides in length.

In certain exemplary embodiments, the C9ORF72 mRNA is C9ORF72 variant 3, designated as NM_001256054.2.

In certain exemplary embodiments, the agent prevents ribosome binding to the C9ORF72 mRNA.

In certain exemplary embodiments, the agent inhibits translation of a C9ORF72 GGGGCC repeat expansion.

In another aspect, a translation modulating agent comprising a polypeptide that binds a gene at or near a translation start site for expanded repeat (e.g., DPR) protein synthesis encoded by the gene to modulate expression of the gene is provided.

In certain exemplary embodiments, the agent is a polypeptide selected from the group consisting of a zinc finger nuclease (ZFN), a transcription-activator like effector nuclease (TALEN), and an RNA-guided nuclease.

In certain exemplary embodiments, the RNA-guided nuclease further comprises one or more guide RNAs.

In certain exemplary embodiments, the guide RNA comprises SEQ ID NO: 4 and/or SEQ ID NO: 5.

In certain exemplary embodiments, the guide RNAs of SEQ ID NO: 4 and SEQ ID NO: 5 flank the C9ORF72 gene region of SEQ ID NO: 6.

In certain exemplary embodiments, a translation start site for expanded repeat (e.g., DPR) protein synthesis is at or near a repeat expansion region selected from the group consisting of CAG, CGG, and GGGGCC. The repeat expansion region may optionally be associated with a disease or disorder selected from the group consisting of spinocerebellar ataxia type 3, spinocerebellar ataxia type 8, myotonic dystrophy type 1, fragile X tremor/ataxia syndrome, amyotrophic lateral sclerosis, frontotemporal dementia, and Huntington's disease. The agent may optionally be a nucleic acid sequence that is sufficiently complementary to an mRNA or a gene region within 100 bases of the 5' end of the repeat expansion region to modulate expression of the mRNA, wherein the agent is a polypeptide that binds to an mRNA or a gene region within 100 bases of the 5' end of the repeat expansion region.

In certain exemplary embodiments, the agent disrupts a translation start site for expanded repeat (e.g., DPR) protein synthesis encoded by intron 1 of a C9ORF72 gene or a C9ORF72 mRNA to inhibit C9ORF72 expression. A translation start site for expanded repeat (e.g., DPR) protein synthesis can optionally be upstream of a GGGGCC repeat expansion region in the C9ORF72 gene or the C9ORF72 mRNA. The agent is optionally sufficiently complementary to a region comprising SEQ ID NO: 1 to disrupt a translation initiation start codon. The agent is optionally sufficiently complementary to a region comprising SEQ ID NO: 2 or SEQ ID NO: 3 to disrupt a translation initiation start codon.

In certain exemplary embodiments, the agent comprises an antisense oligonucleotide. The antisense oligonucleotide is optionally sufficiently complementary to a C9ORF72 mRNA to disrupt translation initiation at a translation start site for expanded repeat (e.g., DPR) protein synthesis of the C9ORF72 mRNA. The antisense oligonucleotide optionally comprises one or more modifications, e.g., one or more modifications are selected from the group consisting of a 2'-O-methyl modified nucleotide, a 2'-fluoro modified nucleotide, a nucleotide comprising a 5'-phosphorothioate group, a terminal nucleotide linked to a cholesterol derivative or hydrophobic molecule, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, a morpholino nucleotide, a phosphoramidate, and a non-natural base comprising nucleotide. The antisense oligonucleotide is optionally between about 5 to about 100 nucleotides in length or between about 10 to about 50 nucleotides in length.

In certain exemplary embodiments, the C9ORF72 mRNA is C9ORF72 variant 3, designated as NM_001256054.2.

In certain exemplary embodiments, the agent prevents ribosome binding to the C9ORF72 mRNA.

In certain exemplary embodiments, the agent inhibits translation of a C9ORF72 GGGGCC repeat expansion.

In another aspect, a method of modulating expression of an mRNA comprising a translation start site for expanded repeat (e.g., DPR) protein synthesis or a gene encoding the mRNA, comprising contacting the mRNA or contacting the gene with an agent that disrupts a translation start site for expanded repeat (e.g., DPR) protein synthesis is provided.

In certain exemplary embodiments, the agent is selected from the group consisting of an antisense oligonucleotide, an siRNA, a ZFN, a TALEN, and an RNA-guided nuclease.

In certain exemplary embodiments, the RNA-guided nuclease further comprises one or more guide RNAs.

In certain exemplary embodiments, the guide RNA comprises SEQ ID NO: 4 and/or SEQ ID NO: 5.

In certain exemplary embodiments, the guide RNAs of SEQ ID NO: 4 and SEQ ID NO: 5 flank the C9ORF72 gene region of SEQ ID NO: 6.

In certain exemplary embodiments, a translation start site for expanded repeat (e.g., DPR) protein synthesis is at or near a repeat expansion region selected from the group consisting of CAG, CGG, and GGGGCC.

In certain exemplary embodiments, the repeat expansion region is associated with a disease or disorder selected from the group consisting of spinocerebellar ataxia type 3, spinocerebellar ataxia type 8, myotonic dystrophy type 1, fragile X tremor/ataxia syndrome, amyotrophic lateral sclerosis, frontotemporal dementia, and Huntington's disease.

In certain exemplary embodiments, the agent is a nucleic acid sequence that is sufficiently complementary to an mRNA or gene region within 100 bases of the 5' end of the repeat expansion to modulate expression of the mRNA or wherein the agent is a polypeptide that binds to an mRNA or gene region within 100 bases of the 5' end of the repeat expansion region.

In certain exemplary embodiments, the agent disrupts a translation start site for expanded repeat (e.g., DPR) protein synthesis encoded by intron 1 of the C9ORF72 gene or present in an mRNA to inhibit C9ORF72 expression. The translation start site for expanded repeat (e.g., DPR) protein synthesis is optionally upstream of a GGGGCC repeat expansion in the C9ORF72 gene or mRNA. The agent is optionally sufficiently complementary to a region comprising SEQ ID NO: 1, SEQ ID NO: 2 or SEQ ID NO:3 to disrupt a translation initiation start codon.

In certain exemplary embodiments, the agent comprises an antisense oligonucleotide. The antisense oligonucleotide is optionally sufficiently complementary to a C9ORF72 mRNA to disrupt translation initiation at a translation start site for expanded repeat (e.g., DPR) protein synthesis of the C9ORF72 mRNA. The antisense oligonucleotide optionally comprises one or more modifications such as, e.g., one or more modifications selected from the group consisting of a 2'-O-methyl modified nucleotide, a 2'-fluoro modified nucleotide, a nucleotide comprising a 5'-phosphorothioate group, a terminal nucleotide linked to a cholesterol derivative or hydrophobic molecule, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, a morpholino nucleotide, a phosphoramidate, and a non-natural base comprising nucleotide.

In certain exemplary embodiments, the antisense oligonucleotide is between about 5 to about 100 nucleotides in length or is between about 10 to about 50 nucleotides in length.

In certain exemplary embodiments, the C9ORF72 mRNA is C9ORF72 variant 3, designated as NM_001256054.2.

In certain exemplary embodiments, the agent prevents ribosome binding to the C9ORF72 mRNA.

In certain exemplary embodiments, the agent inhibits translation of a C9ORF72 GGGGCC repeat expansion.

In another aspect, a method of treating or preventing a disease or disorder associated with a repeat expansion region, comprising administering to a subject in need of such treatment or prevention an agent that disrupts a translation start site for expanded repeat (e.g., DPR) protein synthesis of an mRNA or a translation start site for expanded repeat (e.g., DPR) protein synthesis encoded by a gene is provided.

In certain exemplary embodiments, the agent is selected from the group consisting of an antisense oligonucleotide, an siRNA, a ZFN, a TALEN, and an RNA-guided nuclease.

In certain exemplary embodiments, a translation start site for expanded repeat (e.g., DPR) protein synthesis is at or near a repeat expansion region selected from the group consisting of CAG, CGG, and GGGGCC.

In certain exemplary embodiments, the repeat expansion region is associated with a disease or disorder selected from the group consisting of spinocerebellar ataxia type 3, spinocerebellar ataxia type 8, myotonic dystrophy type 1, fragile X tremor/ataxia syndrome, amyotrophic lateral sclerosis, frontotemporal dementia, and Huntington's disease.

In certain exemplary embodiments, the agent is a nucleic acid sequence that is sufficiently complementary to an mRNA or gene region within about 100 bases of the 5' end of the repeat expansion region to inhibit translation from the mRNA or the agent is a polypeptide that binds to an mRNA or gene region within 100 bases of the 5' end of the repeat expansion region.

In certain exemplary embodiments, the agent disrupts a translation start site for expanded repeat (e.g., DPR) protein synthesis encoded by intron 1 of a C9ORF72 gene or disrupts a translation start site for expanded repeat (e.g., DPR) protein synthesis of an mRNA transcribed from intron 1 of the C9ORF72 gene to inhibit C9ORF72 expression. The translation start site for expanded repeat (e.g., DPR) protein synthesis is optionally upstream of a GGGGCC repeat expansion region in the C9ORF72 gene or the mRNA. The agent is optionally sufficiently complementary to a region comprising SEQ ID NO: 1 to disrupt a translation initiation start codon. The agent is optionally sufficiently complementary to a region comprising SEQ ID NO: 2 or SEQ ID NO: 3 to disrupt a translation initiation start codon.

In certain exemplary embodiments, the agent comprises an antisense oligonucleotide. the antisense oligonucleotide is optionally sufficiently complementary to a C9ORF72 mRNA to disrupt translation initiation at a translation start site for expanded repeat (e.g., DPR) protein synthesis of the C9ORF72 mRNA. The antisense oligonucleotide optionally comprises one or more modifications such as, e.g., one or more modifications selected from the group consisting of a 2'-O-methyl modified nucleotide, a 2'-fluoro modified nucleotide, a nucleotide comprising a 5'-phosphorothioate group, a terminal nucleotide linked to a cholesterol derivative or hydrophobic molecule, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, a morpholino nucleotide, a phosphoramidate, and a non-natural base comprising nucleotide.

In certain exemplary embodiments, the antisense oligonucleotide is between about 5 to about 100 nucleotides in length or is between about 10 to about 50 nucleotides in length.

In certain exemplary embodiments, the C9ORF72 mRNA is C9ORF72 variant 3, designated as NM_001256054.2.

In certain exemplary embodiments, the agent prevents ribosome binding to the C9ORF72 mRNA.

In certain exemplary embodiments, the agent inhibits translation of the C9ORF72 GGGGCC repeat expansion.

In certain exemplary embodiments, the expanded repeat protein is selected from the group consisting of: poly(GA), poly(GR), poly(GP), poly(PA), and poly(PR).

In certain exemplary embodiments, the expanded repeat protein is poly(GA).

In another aspect, a method of suppressing translation from a translation start site for expanded repeat (e.g., DPR) protein synthesis of a C9ORF72 mRNA, comprising contacting the C9ORF72 mRNA with an antisense oligonucleotide that is sufficiently complementary to SEQ ID NO: 2 (ACCTGATAAAGATTAACCAGAA) or SEQ ID NO: 3 (TGTAGCAAGCTCTGGAACTCAG) to block translation initiation from TTA of SEQ ID NO: 2 or from CTG of SEQ ID NO: 3, is provided.

In another aspect, a method of suppressing translation from a translation start site for expanded repeat protein synthesis of a C9ORF72 mRNA, comprising contacting the C9ORF72 gene in a cell with an RNA-guided nuclease and one or more guide RNAs, such that the C9ORF72 gene region of SEQ ID NO: 6 is excised, is provided In certain exemplary embodiments, the guide RNAs comprise SEQ ID NO: 4 and/or SEQ ID NO: 5.

BRIEF DESCRIPTION OF THE DRAWINGS

The foregoing and other features and advantages of the present disclosure will be more fully understood from the following detailed description of illustrative embodiments taken in conjunction with the accompanying drawings.

FIG. 1 discloses SEQ ID NOS 8 and 9, respectively, in order of appearance.

FIG. 7 discloses SEQ ID NO: 10.

FIG. 8A shows the generation of different types of neuronal cells from patient-derived iPSCs for use in testing inhibitors described herein. FIG. 8B shows the generation of mice harboring human C9ORF72 repeats for use in testing one or more inhibitors described herein.

FIG. 9A depicts a schematic of the C9ORF72 gene and the deleted regions via CRISPR editing. FIG. 9B shows that deletion of the 86 nucleotides 5' to the GGGGCC repeat region does not affect expression of the V1, V2, and V3 C9ORF72 transcripts, and this isogenic C9ORF72 iPSC line with 86 nucleotides deletion is denoted by KO-7.

FIG. 12 discloses SEQ ID NO: 11.

FIG. 13 discloses SEQ ID NOS 12-20, respectively, in order of appearance.

DETAILED DESCRIPTION

Figure 1:
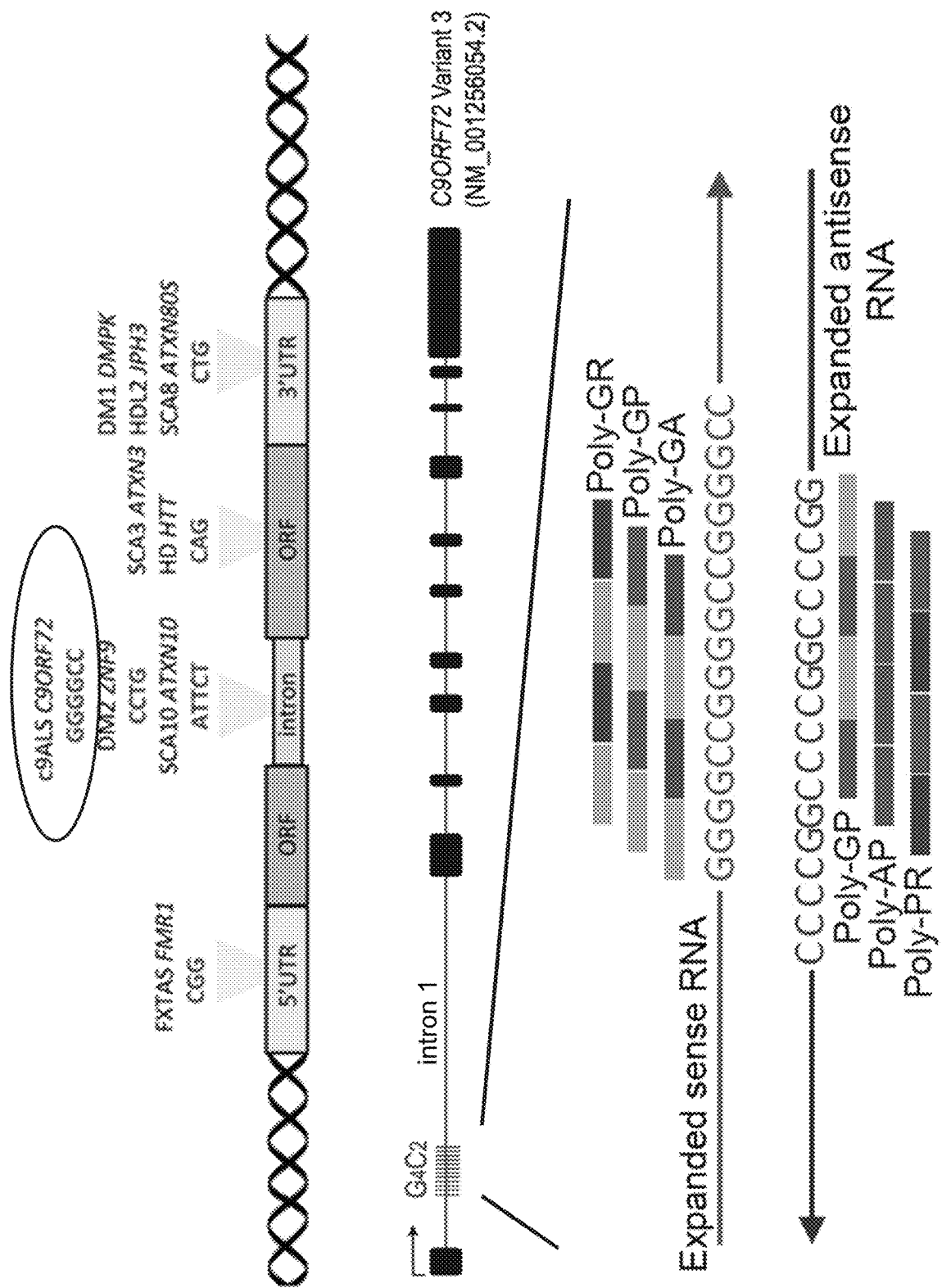
FIG. 1 depicts a schematic of known nucleotide repeat types, there general location in an mRNA, and the diseases they are associated with. Also depicted is a schematic of the C9ORF72 variant 3 transcript and dipeptide repeat (DPR) proteins that are expressed from the sense and antisense RNA of the C9ORF72 gene with the GGGGCC repeat expansion.
Figure 2B:
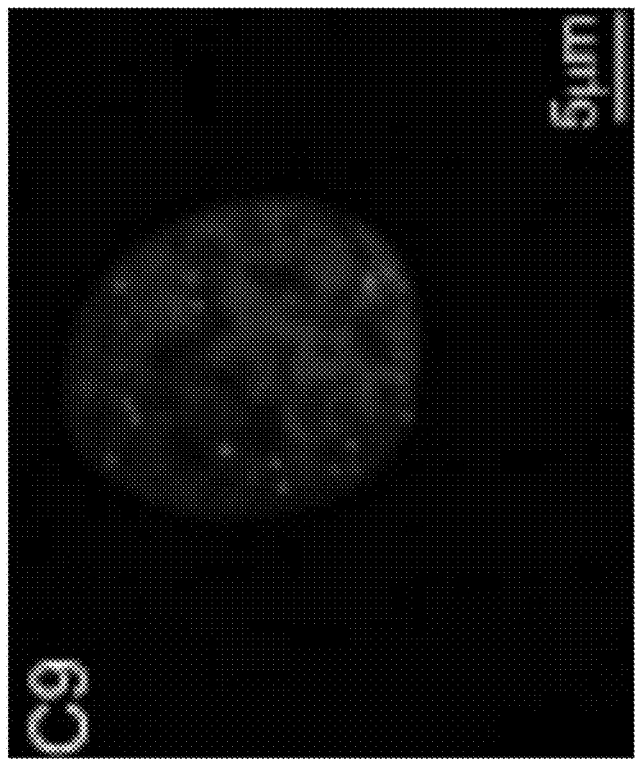
FIG. 2A-FIG. 2B depict cell staining for the GGGGCC DPR aggregates (FIG. 2A) and GGGGCC RNA aggregates (FIG. 2B) derived from the C9ORF72 expanded repeats.
Figure 2A:
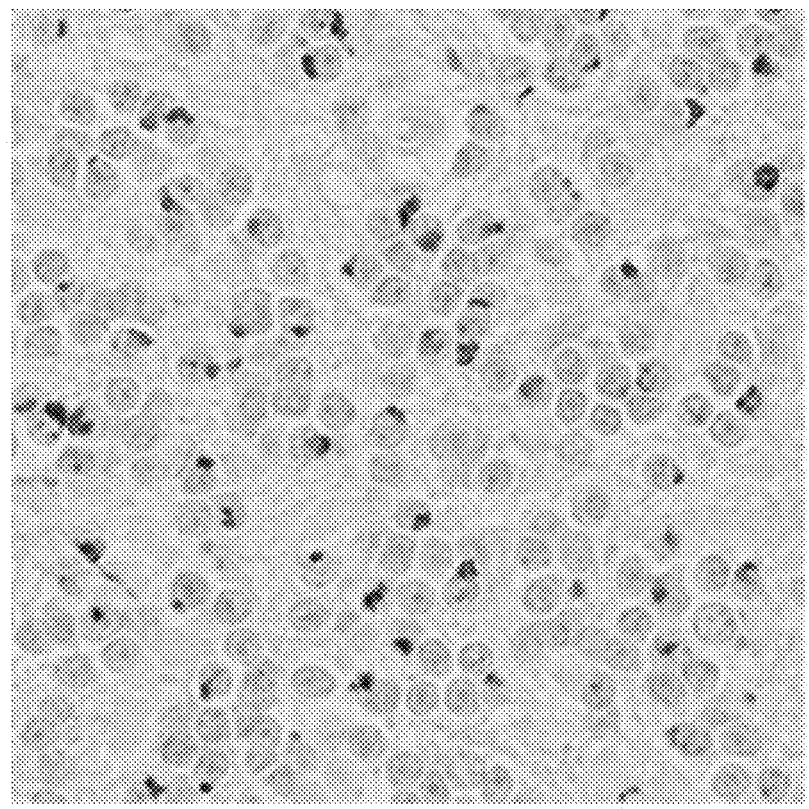
Figure 3:
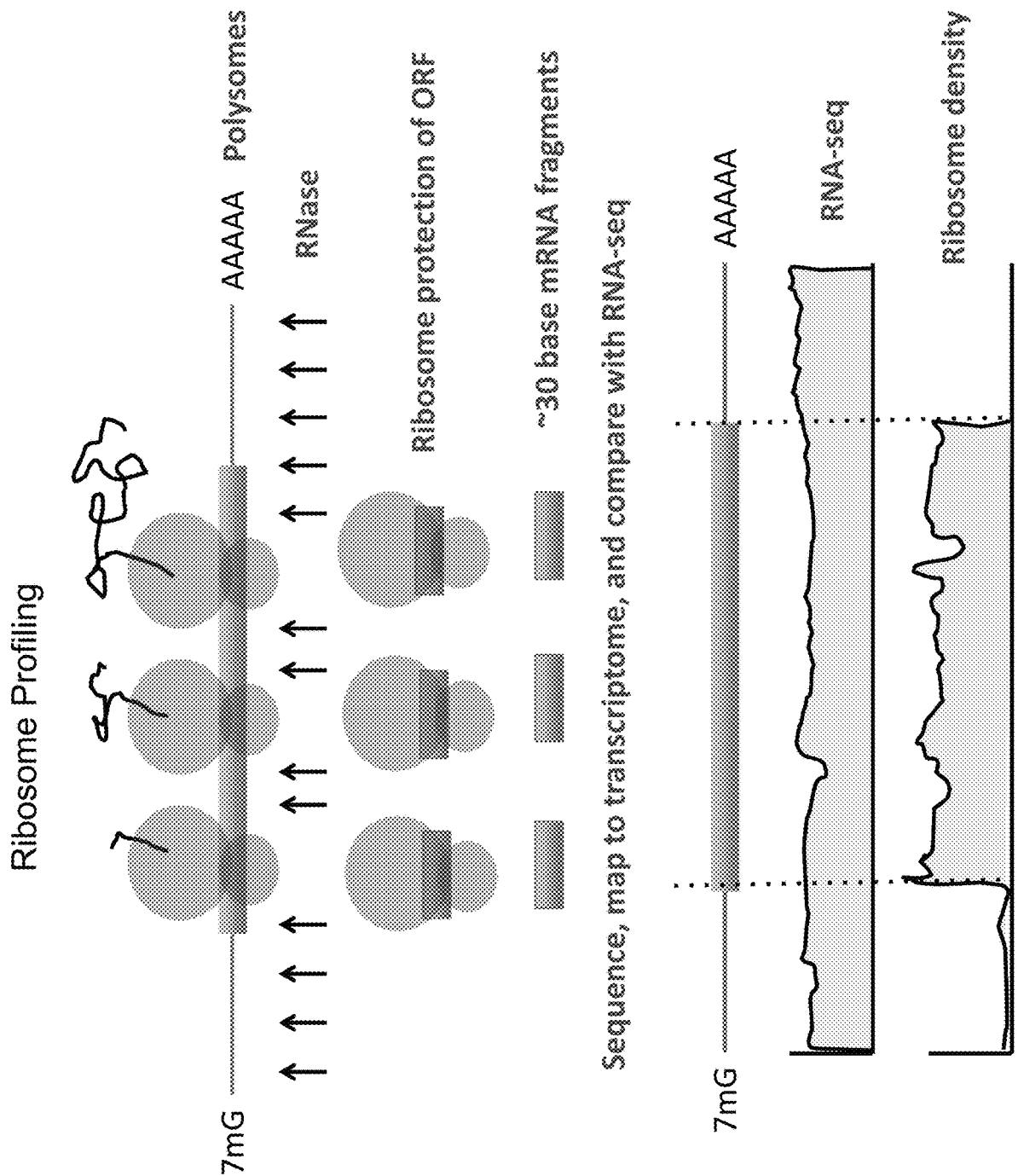
FIG. 3 depicts a general schematic of ribosomal profiling.
Figure 4:
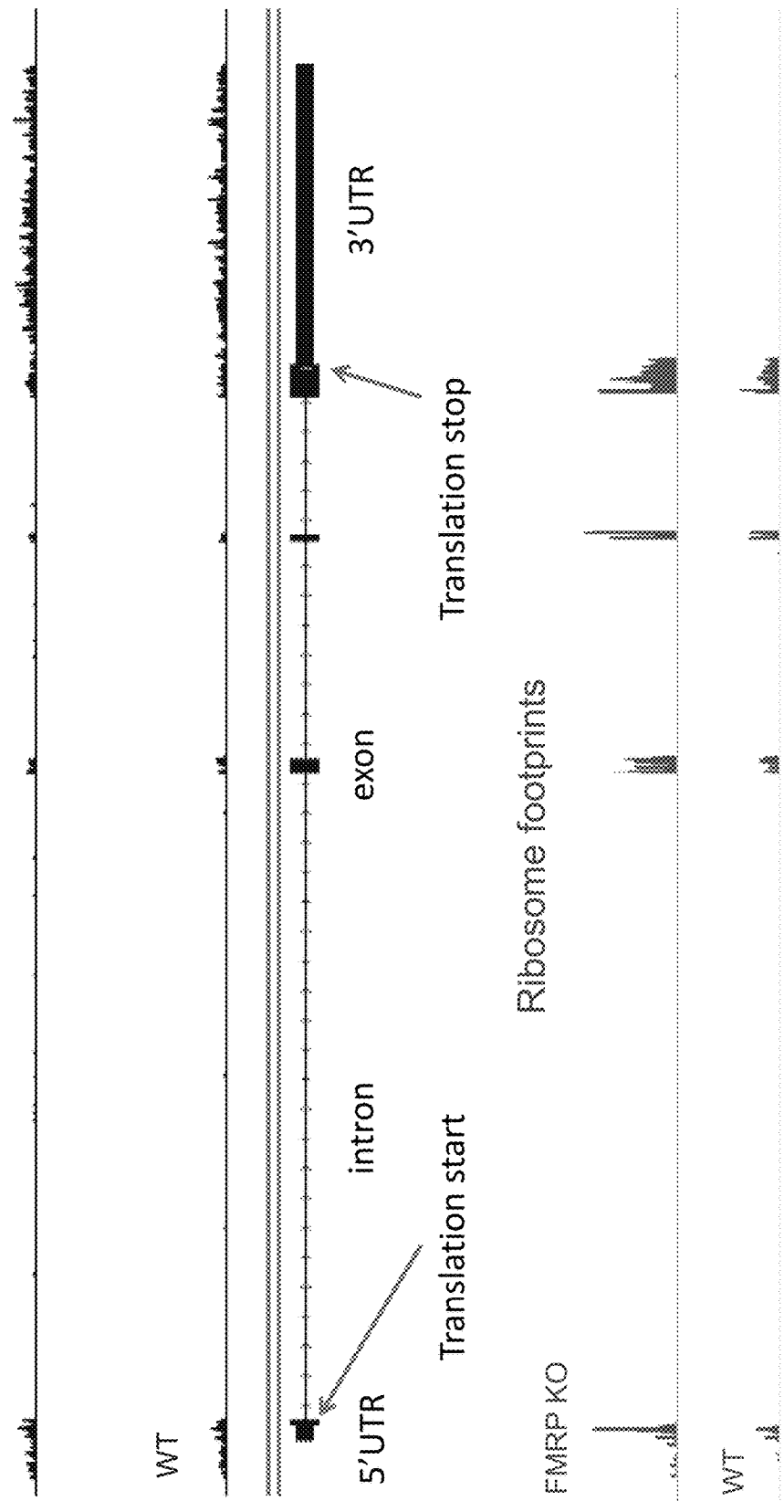
FIG. 4 illustrates an example of RNA-seq and ribosomal profiling for an mRNA in normal and FmR1 knockout (KO mice). It is intended to demonstrate the ribosome profiling technique only.
Figure 5:
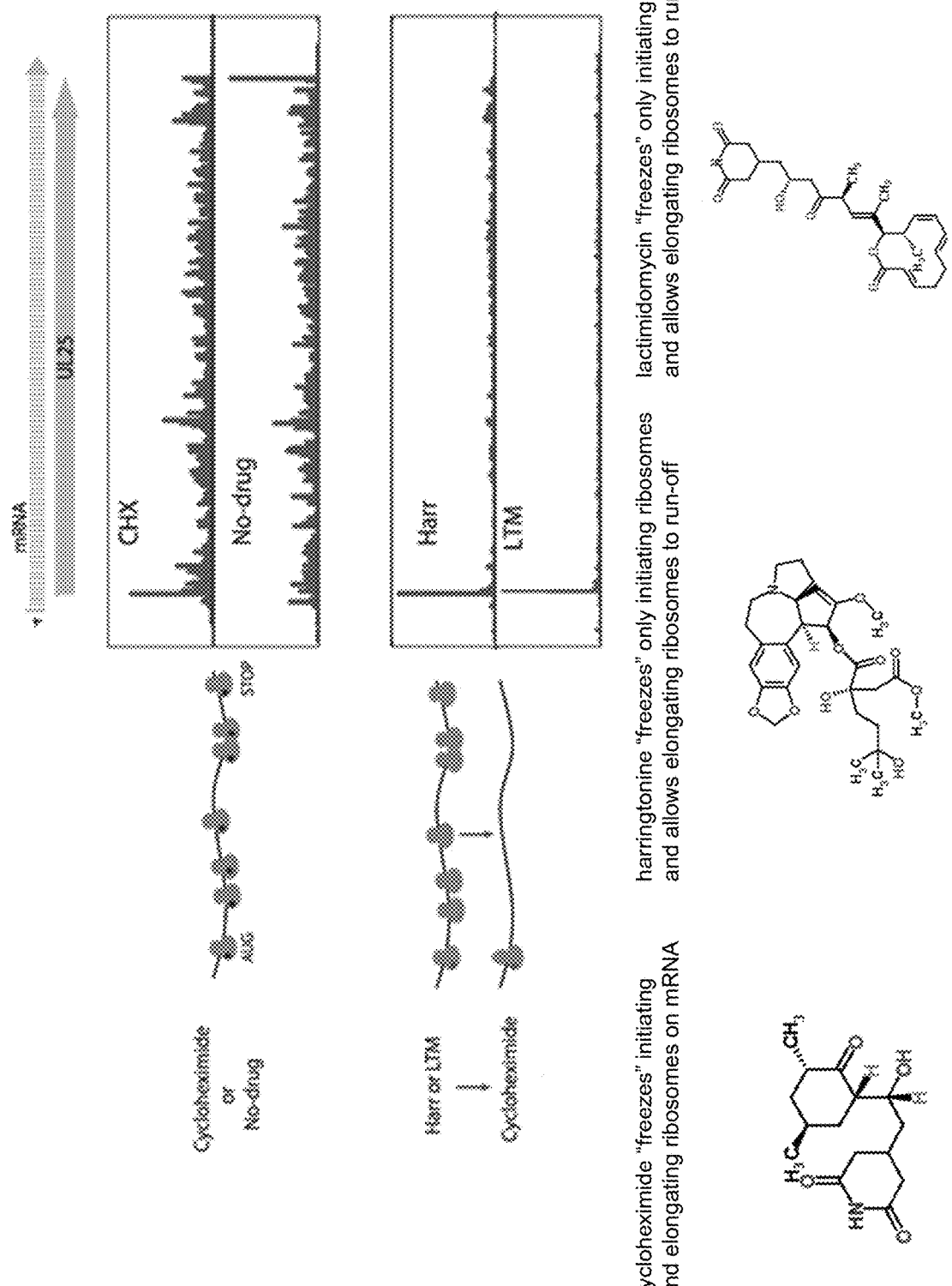
FIG. 5 schematically depicts ribosomal profiling, and show the effect of each of cycloheximide, harringtonine, and lactimidomycin on translation.
Figure 6:
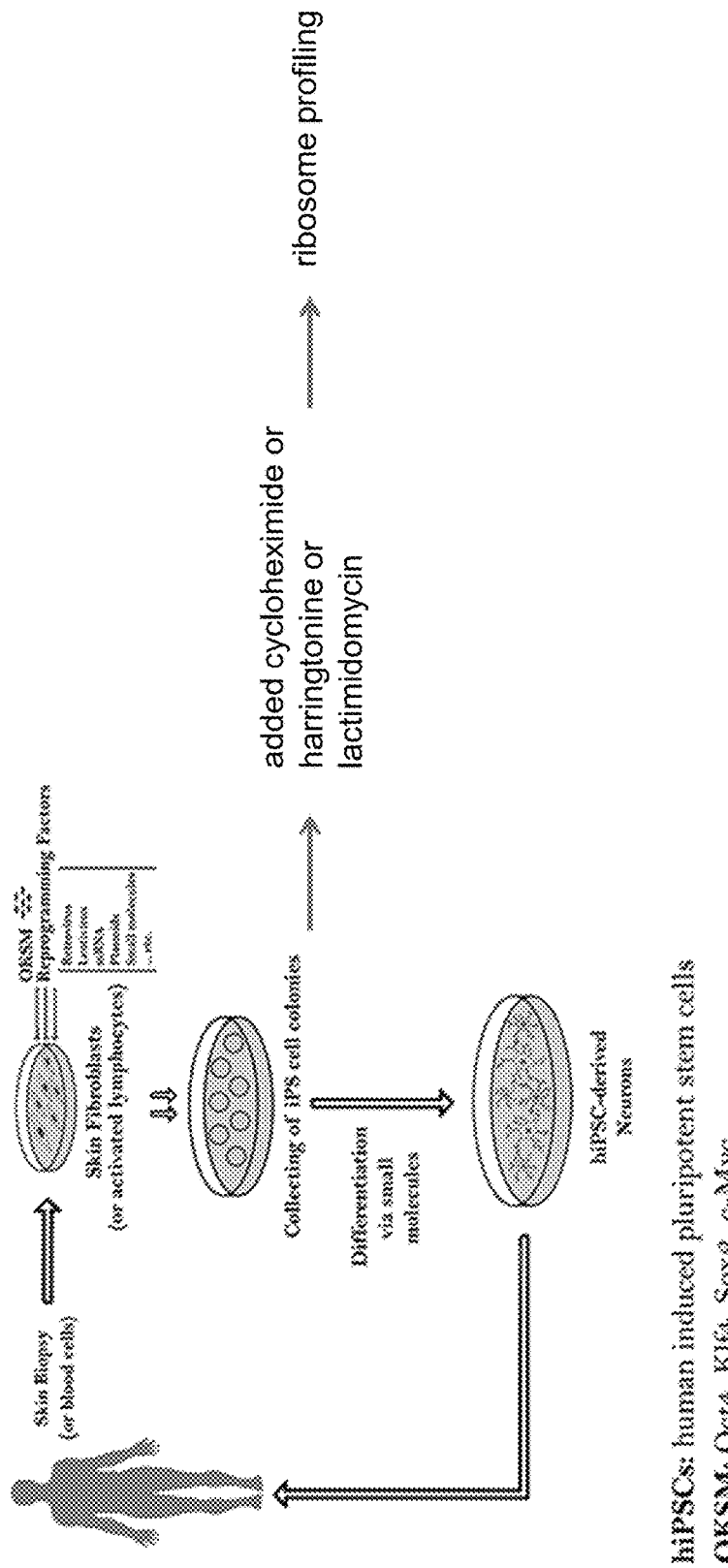
FIG. 6 schematically depicts samples used to perform ribosomal profiling according to particular embodiments. Human iPSCs from normal and diseased patients were used.

Inhibitors that disrupt one or more translation start sites for expanded repeat (e.g., DPR) protein synthesis are provided. Methods and compositions for treating diseases and/or disorders that are associated with CUG, UUA or other start codon-initiated translation of toxic repeat proteins are also provided.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the disclosure may be more readily understood, certain terms are first defined.

As used herein, the term "expanded repeat" refers to repeated DNA sequences that may be present in a genome, corresponding mRNAs that can be transcribed from the repeated DNA sequences, as well as corresponding polypeptides translated from the mRNAs.

Expanded repeats can vary in size from a single nucleotide to an entire gene. Expanded repeats can comprise tandem repeats, interspersed repetitive DNA, or transposable repeat elements. Tandem repeats are often associated with disease syndromes including, but not limited to: bulbospinal neuronopathy; spinocerebellar ataxia (SCA) types 1, 2, 3, 6, 7, 8, 10, 12 and 17; oculopharyngeal muscular dystrophy (OPMD); spastic paraplegia (FSP2); dentatorubral-pallidoluysian atrophy (DRPLA); Huntington's disease types 1 and 2; Baltic myoclonus, fragile chromosome sites (e.g., fragile X syndrome, fragile XE mental retardation, fragile X tremor/ataxia syndrome and the like); Friedreich's ataxia; ataxia, tremor and cognitive decline; myotonic dystrophy (DM1 and DM2); proximal myotonic myopathy; facioscapulohumeral (FSH) dystrophy; amyotrophic lateral sclerosis (ALS); frontotemporal dementia (FTD); spinal and bulbar muscular atrophy; and dentatorubropalliduysian atrophy.

In certain embodiments, an expanded repeat comprises a three-nucleotide repeat, a four-nucleotide repeat, a five-nucleotide repeat, or a six-nucleotide repeat. Nucleotide repeats can include, but are not limited to, the following: $_p$(CCG)n repeats, $_p$(CAG)$_n$ repeats, $_p$(CTG)$_n$ repeats, $_p$(GCG)$_n$ repeats, $_p$(AAG)$_n$ repeats, unstable simple tandem repeats, replications, and expansions in untranslated regions of mRNA.

In certain exemplary embodiments, an expanded repeat comprises a three nucleotide repeat that is optionally translated into a peptide comprising one or more single peptide repeat regions. In other exemplary embodiments, an expanded repeat comprises a six nucleotide repeat that is optionally translated into a peptide comprising one or more dipeptide repeat (e.g., DPR) regions.

As used herein, a "translation start site for expanded repeat protein synthesis" refers to a non-canonical translation start site that is located at or near an expansion repeat region of an mRNA, or the corresponding region of a gene that encodes the mRNA. Exemplary a translation start site for expanded repeat protein synthesis include, but are not limited to, TTA or CTG (or UUA or CUG in a corresponding mRNA).

As used herein, a "translation modulating agent" refers to an agent that modulates (i.e., increases or decreases) translation of a target mRNA, an agent that modulates (i.e., increases or decreases) transcription of a target gene encoding a target mRNA, or an agent that modulates (i.e., increases or decreases) the level of a target gene (e.g., by increasing a target gene copy or functionally inactivating a target gene), e.g., in a cell. Exemplary translation modulating agents include translation start sites for expanded repeat protein synthesis inhibitors.

As used herein, an "expanded repeat protein synthesis inhibitor" refers to an agent that: 1) functionally inactivates a translation start site for expanded repeat protein synthesis-encoding gene; 2) disrupts transcription of a translation start site for expanded repeat protein synthesis-encoding gene into one or more one or more translation start sites for expanded repeat synthesis-containing mRNAs; and/or 3) disrupts translation of a translation start site for expanded repeat protein synthesis-containing mRNA. Inhibitors of translation start sites for expanded repeat protein synthesis include, but are not limited to, antisense RNAs, RNAi agents, genome editing nucleases, guide RNAs and the like, as discussed further herein.

As used herein, an "expansion repeat region" or "repeat expansion region" refers to a portion of a gene (or a portion of one or more mRNAs) that includes repeats of particular nucleotide sequences, i.e., "nucleotide repeats." Exemplary nucleotide repeats include, but are not limited to, CGG, ATTCT, CCTG, GGGGCC, CAG, CTG and the like. Nucleotide repeats are present in increased copies in a gene having an expansion repeat region or a repeat expansion region relative to the number of copies in a wild-type or non-expanded gene. The number of repeats present in an expansion repeat region or a repeat expansion region may be, for example, about 1-10, about 10-100, about 100-1000, or >about 1000 repeats.

Certain embodiments of the disclosure are directed to the treatment of one or more expanded repeat-associated diseases and/or disorders. By "treatment of an expanded repeat-associated disease and/or disorder" is meant the use of an inhibitor described herein to disrupt a translation start site for expanded repeat (e.g., DPR) protein synthesis in a subject, in order to reduce or eliminate one or more symptoms of the disease and/or disorder in the subject.

Target Sequence

The present disclosure provides compositions comprising inhibitors of one or more translation start sites for expanded repeat (e.g., DPR) protein synthesis, and methods of using inhibitors of one or more translation start sites for expanded repeat (e.g., DPR) protein synthesis. In certain embodiments, a translation start site for expanded repeat protein synthesis is associated with the expression of dipeptide repeat (DPR) proteins. Accordingly, the present disclosure provides compositions and methods for inhibiting the expression of DPR proteins or other repeat proteins. A translation start site for expanded repeat (e.g., DPR) protein synthesis-containing nucleic acids (e.g., transcripts and the genes that encode them) may be targeted using one or more compositions and/or methods of the present disclosure.

Certain methods and compositions for inhibiting C9ORF72 expression have been described. (See U.S. Pat. No. 9,605,263, incorporated herein by reference.)

TABLE 1

Exemplary target sequences.

| Target | Sequence |
|---|---|
| C9ORF72 intron 1 segment | GTGTGTGTTTTTGTTTTTCCACCCTCTCTCCCCACT ACTTGCTCTCACAGTACTCGCTGAGGGTGAACAAGA AAAGACCTGATAAAGATTAACCAGAAGAAAACAAGG AGGGAAACAACCGCAGCCTGTAGCAAGCTCTGGAAC TCAGGAGTCGCGCGCTA*GGGGGCCGGGGCCGGGGCC GGGGC* (SEQ ID NO: 1) |
| Target sequence 1 | ACCTGATAAAGATTAACCAGAA (SEQ ID NO: 2) |
| Target sequence 2 | TGTAGCAAGCTCTGGAACTCAG (SEQ ID NO: 3) |

SEQ ID NOs: 2 and 3 refer to the sequences recited above in Table 1 as target sequence 1 and target sequence 2, optionally including approximately 10 nucleotides on either side, which overlap the two start codons of interest. SEQ ID NO: 2 refers to a nucleic acid sequence that overlaps the TTA sequence of SEQ ID NO: 1. SEQ ID NO: 3 refers to a nucleic acid sequence that overlaps the CTG sequence of SEQ ID NO: 1.

Compositions of the present disclosure are designed to inhibit, either directly or indirectly, translation initiation from one or both of the translation start sites upstream of the GGGGCC repeat of the C9ORF72 gene.

Direct inhibition of translation initiation can be achieved using a translational inhibitor as described herein that binds to a region at or near a repeat expansion in an mRNA. In certain exemplary embodiments, the translational inhibitor covers, or partially covers one or more translation start sites for expanded repeat (e.g., DPR) protein synthesis described herein such that translation initiation is inhibited. Exemplary translational inhibitors that mediate direct translational inhibition include, but are not limited to, antisense oligonucleotides and RNAi agents, such as siRNAs, miRNAs, and shRNAs.

Indirect inhibition of translation initiation can be achieved using a translational inhibitor described herein that binds to a region at or near a repeat expansion in a gene. In certain exemplary embodiments, the translational inhibitor edits the genome at one or more locations that encode for a translation start site for expanded repeat (e.g., DPR) protein synthesis identified in the present disclosure such that translation initiation of the transcribed mRNA is inhibited. Exemplary translational inhibitors that mediate indirect translational inhibition include, but are not limited to, genome-editing nucleases, such as clustered regularly interspaced short palindromic repeats (CRISPR)/Cas9 and their corresponding guide RNAs (gRNAs), transcription activator-like effector nucleases (TALENs), or zinc finger nucleases (ZFNs).

Dipeptide Repeat Region (DPR) Proteins

As used herein, a "dipeptide repeat region protein" or "dipeptide repeat protein" or "DPR protein" or "expanded repeat protein" refers to proteins that are expressed from the nucleotide repeat regions of mRNA transcripts associated with repeat expansion diseases or disorders. Exemplary DPR proteins include, but are not limited to, the DPR proteins expressed from the hexanucleotide GGGGCC repeat located in intron 1 of C9ORF72. These DPR proteins are translated from all six open reading frames in either the sense or antisense direction of the GGGGCC nucleotide repeat. The DPR proteins include poly glycine-alanine or poly(GA), poly glycine-arginine or poly(GR), poly proline-alanine or poly(PA), poly proline-arginine or poly(PR), and poly glycine-proline or poly(GP). Poly(GP) is generated from both the sense and antisense direction. Poly(GR) and poly(GA) are generated from the sense direction. Poly(PA) and poly(PR) are generated from the antisense direction. A schematic of C9ORF72 and the DPR proteins expressed from the GGGGCC nucleotide repeat region is depicted in FIG. 1. The C9ORF72 DPR proteins are further described in Freibaum et al. 2017. Front Mol Neurosci. 10: 35.

Repeat Expansion Diseases and Disorders

As used herein, a "repeat expansion disease or disorder" refers to diseases or disorders that are associated with repeat expansion regions in genes and the mRNA they encode. Repeat expansion diseases or disorders may be further associated with a translation start site for expanded repeat (e.g., DPR) protein synthesis located at or near a repeat expansion region. The repeat expansion diseases or disorders may be caused, in part, by protein gain-of-function and mRNA gain-of-function effects resulting from the repeat expansion regions. The repeat expansion diseases or disorders may be further caused, in part, by the translation of toxic DPR proteins derived from a translation start site for expanded repeat (e.g., DPR) protein synthesis of repeat expansion genes and the mRNA they encode. Exemplary repeat expansion diseases or disorders include, but are not limited to, neurological diseases and disorders, such as ALS, FTD, Huntington's disease, spinocerebellar ataxia type 3, spinocerebellar ataxia type 8, myotonic dystrophy type 1, and/or fragile X tremor/ataxia syndrome (see e.g., Wojceichowska et al. Nucleic Acids Research, 2014. 42:11849-11864.)

Antisense Oligonucleotides

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). An RNA nucleotide refers to a single ribonucleotide. The term "DNA" or "DNA molecule" or "deoxyribonucleic acid molecule" refers to a polymer of deoxyribonucleotides. A DNA nucleotide refers to a single deoxyribonucleotide. As used herein, the term "DNA-like" refers to a conformation of, e.g. a modified nucleoside or nucleotide which is similar to the conformation of a corresponding unmodified DNA unit. For example, a DNA-like nucleotide may refer to a conformation of a modified deoxyribonucleotide similar to a corresponding unmodified deoxyribonucleotide. Examples of DNA-like nucleotides include, without limitation, e.g., 2'-deoxyribonucleotides, 2'-deoxy-2'-substituted arabinonucleotides (e.g., 2'-deoxy-2'-fluoroarabinonucleotides, also known in the art as 2'F-ANA or FANA), and corresponding phosphorothioate analogs. As used herein, the term "RNA-like" refers to a conformation of, e.g. a modified nucleoside or nucleotide which is similar to the conformation of a corresponding unmodified RNA unit. RNA-like conformations may adopt an A-form helix while DNA-like conformations adopt a B-form helix. Examples RNA-like nucleotides include, without limitation, e.g., 2'-substituted-RNA nucleotides (e.g., 2'-fluoro-RNA nucleotides also known in the art as 2'F-RNA), locked nucleic acid (LNA) nucleotides (also known in the art as bridged nucleic acids or bicyclic nucleotides), 2'-fluoro-4'-thioarabinonucleotide (also known in the art as 4'S-FANA nucleotides), 2'-O-alkyl-RNA, and corresponding phosphorothioate analogs.

DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary modified nucleotides are modified at any position so as to alter certain chemical properties of the nucleotide yet retain the ability of the modified nucleotide to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Modified nucleotides also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotides such as those described in Herdewijn, Antisense Nucleic Acid Drug Dev., 2000 Aug. 10(4):297-310.

Modified nucleotides may also comprise modifications to the sugar portion of the nucleotides. For example, the 2' OH-group may be replaced by a group selected from H, OR, R, F, Cl, Br, I, SH, SR, NH2, NHR, NR2, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11 (5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

As used herein, the terms "unmodified nucleotide" or "non-modified nucleotide" refers to a nucleotide composed of naturally occurring nucleobases, sugar moieties, and internucleoside linkages. In some embodiments, a non-modified nucleotide is an RNA nucleotide (i.e. β-D-ribonucleoside) or a DNA nucleotide (i.e. (3-D-deoxyribonucleoside).

The term "oligonucleotide" refers to a short polymer of nucleotides and/or modified nucleotides. As discussed above, the oligonucleotides may be linked with linkages which result in a lower rate of hydrolysis as compared to an oligonucleotide linked with phosphodiester linkages. For example, the nucleotides of the oligonucleotide may comprise methylenediol, ethylene diol, oxymethylthio, oxyethylthio, oxycarbonyloxy, phosphorodiamidate, phosphoroamidate, and/or phosphorothioate linkages. Alterations or modifications of the oligonucleotide can further include addition of non-nucleotide material, such as to the end(s) of the oligonucleotide or internally (at one or more nucleotides of the oligonucleotide).

As used herein, the term "antisense compound" refers to a compound which is capable of inhibiting or "silencing" the expression of a target gene. In certain embodiments, the antisense compound is capable of preventing complete processing (e.g., the full translation and/or expression) of an mRNA molecule through a post-transcriptional silencing mechanism. Antisense compounds include, without any limitation, antisense oligonucleotides, gapmer molecules, and dual-function oligonucleotides as well as precursors thereof. In some embodiments, the antisense compound blocks translation initiation of a target mRNA. For example, an antisense compound of the present disclosure can be an antisense oligonucleotide that blocks translation initiation from one or both of the novel translation start sites for expanded repeat (e.g., DPR) protein synthesis of the C9ORF72 or FRM1 transcript.

The term "gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments." "Chimeric antisense compound" means an antisense compound that has at least two chemically distinct regions.

As used herein, the term "target gene" is a gene whose expression is to be substantially inhibited or "silenced." This silencing can be achieved by RNA silencing, e.g., by cleaving mRNA corresponding to a target gene or translational repression of the target gene. The term "non-target gene" is a gene whose expression is not to be substantially silenced. For example, a suitable target gene is C9ORF72 or FMR1, and a non-target gene is a gene that is not C9ORF72 or FMR1. In one embodiment, the polynucleotide sequences of the target and non-target gene (e.g., mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g., an orthologue or paralogue) of the target gene.

The term "antisense activity" means any detectable or measurable activity attributable to the hybridization of an antisense compound to its target nucleic acid. In some embodiments, antisense activity is a decrease in the amount or expression of a target nucleic acid or protein encoded by such target nucleic acid. "Antisense compound" means an oligomeric compound that is capable of undergoing hybridization to a target nucleic acid through hydrogen bonding. As used herein, "antisense oligonucleotide" means a single-stranded oligonucleotide having a nucleobase sequence that permits hybridization to a corresponding region or segment of a target nucleic acid.

The term "antisense inhibition" means reduction of target nucleic acid levels or target protein levels in the presence of an antisense compound having a target-recognition sequence that is sufficiently complementary to a target nucleic acid compared to target nucleic acid levels or target protein levels in the absence of the antisense compound. A target nucleic acid can be any nucleic acid. For example, an exemplary target nucleic acid can be a C9ORF72 or an FMR1 transcript.

The term "target-recognition sequence" refers to the portion of an antisense compound that recognizes a target nucleic acid. The target-recognition sequence has a nucleobase sequence that permits hybridization to a corresponding region or segment of a target nucleic acid.

As used herein, the "5' end," as in the 5' end of the open reading frame of an C9ORF72 or FMR1 transcript, refers to the 5' terminal nucleotides of the open reading frame of the C9ORF72 or FMR1 transcript. As used herein, the "3' end,"

as in the 3' end of the open reading frame of an C9ORF72 or FMR1 transcript, refers to the 3' terminal nucleotides of the open reading frame of the C9ORF72 or FMR1 transcript.

The term "conserved region" refers to a portion, or portions, of a nucleic acid sequence that is conserved, i.e. a portion, or portions of the nucleic acid sequence having a similar or identical sequence across species. A conserved region may be computationally identified, e.g., using any sequence alignment software available in the art.

As used herein, the term "sufficiently complementary" means that an RNA silencing agent has a sequence (e.g., an antisense oligonucleotide or RNAi having a target-recognition sequence) which is sufficient to bind the desired target mRNA (e.g., an C9ORF72 or FMR1 transcript), and to block translation initiation of the target mRNA. For example, a target-recognition sequence with at least about 70%, about 80%, about 90%, or about 95% complementarity to a target nucleic acid sequence (e.g., a portion of an C9ORF72 or FMR1 transcript) may be sufficiently complementary to trigger silencing of the C9ORF72 or FMR1 transcript. The term "perfectly complementary" refers to, e.g., a target-recognition sequence with 100% complementarity to a target nucleic acid sequence. Complementary nucleic acid molecules hybridize to each other. The term "hybridization" means the annealing of complementary nucleic acid molecules. In certain embodiments, complementary nucleic acid molecules include an antisense compound and a target nucleic acid.

The term "about" or "approximately" means within 20%, such as within 10%, within 5%, or within 1% or less of a given value or range.

As used herein, "administer" or "administration" refers to the act of injecting or otherwise physically delivering a substance as it exists outside the body (e.g., an antisense compound provided herein) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or a symptom thereof, is being managed or treated, administration of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symptoms, e.g., damage to the involved tissues and airways.

As used herein, the term "composition" is intended to encompass a product containing the specified ingredients (e.g., an antisense compound provided herein) in, optionally, the specified amounts, as well as any product which results, directly or indirectly, from combination of the specified ingredients in, optionally, the specified amounts.

"Effective amount" means the amount of active pharmaceutical agent (e.g., an antisense compound of the present disclosure) sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject is can be a mammal, such as a non-primate (e.g., cows, pigs, horses, cats, dogs, rats, etc.) or a primate (e.g., monkey or human). In certain embodiments, the term "subject," as used herein, refers to a vertebrate, such as a mammal. Mammals include, without limitation, humans, non-human primates, wild animals, feral animals, farm animals, sports animals, and pets. In one embodiment, the subject is a mammal, such as a human, having a repeat-associated disease or disorder (e.g., ALS, FTD, Huntington's disease). In another embodiment, the subject is a mammal, such as a human, that is at risk for developing a repeat-associated disease or disorder.

As used herein, the term "therapy" refers to any protocol, method and/or agent that can be used in the prevention, management, treatment and/or amelioration of a disease or a symptom related thereto, such as a repeat-associated disease or disorder (e.g., ALS, FTD, Huntington's disease). In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, such as a repeat-associated disease or disorder known to one of skill in the art such as medical personnel. In other embodiments, the terms "therapies" and "therapy" refer to a biological therapy, supportive therapy, and/or other therapies useful in the modulation of an immune response to an infection in a subject or a symptom related thereto known to one of skill in the art such as medical personnel.

As used herein, the terms "treat," "treatment" and "treating" refer to the reduction or amelioration of the progression, severity, and/or duration of a disease or a symptom related thereto, such as a repeat-associated disease or disorder, resulting from the administration of one or more therapies (including, but not limited to, the administration of one or more prophylactic or therapeutic agents, such as an antisense oligonucleotide provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

The present disclosure provides an antisense compound that is capable of mediating translational inhibition of at least 50%, at least 55%, at least 60%, at least 65%, at least 70%, at least 75%, at least 80%, at least 85%, at least 90%, at least 95% or more of translation start site for expanded repeat (e.g., DPR) protein synthesis-containing transcripts, such as C9ORF72 and FMR1. In one embodiment, the antisense compound is capable of mediating translational inhibition of at least 80% of translation start site for expanded repeat (e.g., DPR) protein synthesis-containing transcripts. In one embodiment, the antisense compound is capable of mediating translational inhibition of at least 90% of translation start site for expanded repeat (e.g., DPR) protein synthesis-containing transcripts.

In certain embodiments, antisense compounds that is capable of mediating translational inhibition of a translation start site for expanded repeat (e.g., DPR) protein synthesis-containing transcript or portion thereof, have chemically modified subunits arranged in patterns, or motifs, to confer to the antisense compounds properties such as enhanced the inhibitory activity, increased binding affinity for a target nucleic acid, or resistance to degradation by in vivo nucleases.

In some embodiments, an antisense compound of the present disclosure is an antisense oligonucleotide. Chimeric antisense oligonucleotides typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex. In some embodiments, an antisense compound of the present disclosure is a chimeric antisense oligonucleotide having a gapmer motif. In a gapmer an internal region having a plurality of nucleotides that supports RNaseH cleavage is positioned between external regions having a plurality of nucleotides that are chemically distinct from the nucleosides of the internal region.

In some embodiments, the present disclosure provides a synthetic antisense oligonucleotide having a target-recognition sequence that is sufficiently complementary to a translation start site for expanded repeat (e.g., DPR) protein synthesis-containing transcript or portion thereof, to direct translational inhibition of a translation start site for expanded repeat (e.g., DPR) protein synthesis-containing transcript. The target-recognition sequence may be complementary to a translation start site for expanded repeat (e.g., DPR) protein synthesis, such as the novel translation start site for DPR protein synthesis of C9ORF72 of the present disclosure. The target-recognition sequence of the antisense oligonucleotide can be the full length of the antisense oligonucleotide, or a portion thereof. In some embodiments, the antisense oligonucleotide comprises a gapmer motif.

In the case of an antisense compound having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH3 (i.e., OMe), among others), and bicyclic sugar modified nucleosides (such bicyclic sugar modified nucleosides may include those having a 4'-(CH2)n-O-2' bridge, where n=1 or n=2). In some embodiments, each distinct region comprises uniform sugar moieties.

The gapmer motif can be described using the formula "A-B—C", where "A" represents the length of the 5' wing region, "B" represents the length of the gap region, and "C" represents the length of the 3' wing region. As such, in some embodiments, an antisense oligonucleotide of the present disclosure has the formula: A-B—C.

As used herein, a gapmer described as "A-B—C" has a configuration such that the gap segment is positioned immediately adjacent each of the 5' wing segment and the 3' wing segment. Thus, no intervening nucleotides exist between the 5' wing segment and gap segment, or the gap segment and the 3' wing segment.

In some embodiments, the 5' wing region represented by "A" comprises from about 0 to about 8 modified nucleotides, e.g., from about 1 to about 6 modified nucleotides. For example, the 5' wing region represented by "A" can be 0, 1, 2, 3, 4, 5, 6, 7, or 8 nucleotides in length. In some embodiments, the 3' wing region represented by "C" comprises about 0 to about 8 modified nucleotides, e.g., from about 1 to about 6 modified nucleotides. For example, the 3' wing region represented by "C" can be 0, 1, 2, 3, 4, 5, 6, 7, or 8 nucleotides in length. In some embodiments, "A" and "C" are the same, in some embodiments, they are different.

In some embodiments, the gap region represented by "B" comprises from about 4 to about 18 DNA nucleotides and/or DNA-like nucleotides, e.g., from about 4 to about 12 DNA nucleotides and/or DNA-like nucleotides. For example, the gap region represented by "B" can be 4, 5, 6, 7, 8, 9, 10, 11, 12, 13, 14, 15, 16, 17, or 18 DNA nucleotides and/or DNA-like nucleotides in length. Thus, an antisense oligonucleotide of the present disclosure having a target-recognition sequence with the formula "A-B—C" include, but are not limited to the following gapmer formats, for example 1-4-1 (i.e., one nucleotide—four nucleotides—one nucleotide), 1-5-1, 1-6-1, 1-7-1, 1-8-1, 1-9-1, 1-10-1, 1-11-1, 1-12-1, 2-4-2, 2-5-2, 2-6-2, 2-7-2, 2-8-2, 2-9-2, 2-10-2, 2-11-2, 2-12-2, 3-4-3, 3-5-3, 3-6-3, 3-7-3, 3-8-3, 3-9-3, 3-10-3, 3-11-3, 3-12-3, 4-4-4, 4-5-4, 4-6-4, 4-7-4, 4-8-4, 4-9-4, 4-10-4, 4-11-4, 4-12-4, 5-4-5, 5-5-5, 5-6-5, 5-7-5, 5-8-5, 5-9-5, 5-10-5, 5-11-5, 5-12-5, 6-4-6, 6-5-6, 6-6-6, 6-7-6, 6-8-6, 6-9-6, 6-10-6, 6-11-6, or 6-12-6.

In certain embodiments, antisense compounds targeted to a translation start site for expanded repeat (e.g., DPR) protein synthesis-containing nucleic acid possess a 3-9-3 gapmer format. In some embodiments, the antisense compound is an antisense oligonucleotide having a target-recognition sequence with the 3-9-3 format that is sufficiently complementary to a translation start site for expanded repeat (e.g., DPR) protein synthesis-containing transcript, or a portion thereof, to direct translational inhibition of a translation start site for expanded repeat (e.g., DPR) protein synthesis-containing transcript by blocking translation initiation. In some embodiments, the target-recognition sequence has the formula "A-B—C", wherein "A" comprises about 3 modified nucleotides, "B" comprises about 9 DNA nucleotides and/or DNA-like nucleotides, and "C" comprises about 3 modified nucleotides. In some embodiments, the target-recognition sequence has the formula "A-B—C", wherein "A" comprises 3 locked nucleotides, "B" comprises 9 DNA nucleotides and/or DNA-like nucleotides, and "C" comprises 3 locked nucleotides. In some embodiments, the target-recognition sequence has the formula "A-B—C", wherein "A" comprises 3 locked nucleotides, "B" comprises 9 DNA-like nucleotides, and "C" comprises 3 locked nucleotides.

In some embodiments, antisense compounds that target a translation start site for expanded repeat (e.g., DPR) protein synthesis-containing nucleic acid possess a "wingmer" motif. The wingmer motif can be described using the formula "X—Y" or "Y—X", where "X" represents the length of the wing region, and "Y" represents the length of the gap region. As such, in some embodiments, an antisense oligonucleotide of the present disclosure has the formula:

X—Y, or

Y—X.

As used herein, a wingmer described as "X—Y" or "Y—X" has a configuration such that the gap segment is positioned immediately adjacent to the wing segment. Thus, no intervening nucleotides exist between the wing segment and the gap segment. Non-limiting examples of wingmer configurations of an antisense compound of the present disclosure include, e.g., 1-10, 1-11, 1-12, 2-9, 2-10, 2-11, 2-12, 3-8, 3-9, 3-10, 3-11, 3-12, 4-7, 4-8, 4-9, 4-10, 4-11, 4-12, 5-6, 5-7, 5-8, 5-9, 5-10, 5-11, or 5-12.

In some embodiments, antisense compounds targeted to a translation start site for expanded repeat (e.g., DPR) protein synthesis-containing nucleic acid possess a gap-widened motif. As used herein, "gap-widened" refers to an antisense compound having a gap segment of 12 or more contiguous DNA nucleotides and/or DNA-like nucleotides adjacent to a wing region. In the case of a gap-widened gapmer, the gapmer comprises a gap region having 12 or more contiguous DNA nucleotides and/or DNA-like nucleotides positioned between and immediately adjacent to the 5' and 3' wing segments. In the case of a gap-widened wingmer, the wingmer comprises a gap region having 12 or more contiguous DNA nucleotides and/or DNA-like nucleotides positioned immediately adjacent to the wing segment.

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a translation start site for expanded repeat (e.g., DPR) protein synthesis-containing nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Antisense compounds provided herein can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F (i.e., 2'-fluoro), 2'-OCH3 (i.e., 2'-O-methyl) and 2'-O(CH2)2OCH3 (i.e., 2'-O-methoxyethyl) substituent groups. The substituent at the 2' position can also be selected from allyl, amino, azido, thio, 0-allyl, 0-C1-C10 alkyl, OCF3, O(CH2)2SCH3, O(CH2)2-O—N(Rm)(Rn), and 0-CH2-C(=O)—N(Rm)(Rn), where each Rm and Rn is, independently, H or substituted or unsubstituted C1-C10 alkyl. 2'-modified nucleotides are useful, for example, 2'-O-methyl RNA, 2'-O-methoxyethyl RNA, 2'-fluoro RNA, and others envisioned by one of ordinary skill in the art.

Examples of bicyclic nucleic acids (BNAs) include without limitation nucleosides comprising a bridge between the 4' and the 2' ribosyl ring atoms. A BNA comprising a bridge between the 4' and 2' ribosyl ring atoms can be referred to as a locked nucleic acid (LNA), and is often referred to as inaccessible RNA. As used herein, the term "locked nucleotide" or "locked nucleic acid (LNA)" comprises nucleotides in which the 2' deoxy ribose sugar moiety is modified by introduction of a structure containing a heteroatom bridging from the 2' to the 4' carbon atoms. The term "non-locked nucleotide" comprises nucleotides that do not contain a bridging structure in the ribose sugar moiety. Thus, the term comprises DNA and RNA nucleotide monomers (phosphorylated adenosine, guanosine, uridine, cytidine, deoxyadenosine, deoxyguanosine, deoxythymidine, deoxycytidine) and derivatives thereof as well as other nucleotides having a 2'-deoxy-erythro-pentofuranosyl sugar moiety or a ribopentofuranosyl moiety. In certain embodiments, antisense compounds provided herein include one or more BNA nucleosides wherein the bridge comprises one of the formulas: 4'-(CH2)-O-2' (LNA); 4'-(CH2)-S-2'; 4'-(CH2)-O-2' (LNA); 4'-(CH2)2-O-2' (ENA); 4'-C(CH3)2-O-2' (see PCT/US2008/068922); 4'-CH(CH3)-O-2' and 4'-CH(CH2OCH3)-O-2' (see U.S. Pat. No. 7,399,845, issued on Jul. 15, 2008); 4'-CH2-N(OCH3)-2' (see PCT/US2008/064591); 4'-CH2-O—N(CH3)-2' (see published U.S. Patent Application US2004-0171570, published Sep. 2, 2004); 4'-CH2-N(R)—O-2' (see U.S. Pat. No. 7,427,672, issued on Sep. 23, 2008); 4'-CH2-C(CH3)-2' and 4'-CH2-C(=CH2)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In some embodiments, antisense compounds provided herein include one or more 2', 4'-constrained nucleotides. For example, antisense compounds provided by the present disclosure include those having one or more constrained ethyl (cEt) or constrained methoxyethyl (cMOE) nucleotides. In some embodiments, antisense compounds provided herein are antisense oligonucleotides comprising one or more constrained ethyl (cEt) nucleotides. The terms "constrained ethyl" and "ethyl-constrained" are used interchangeably.

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

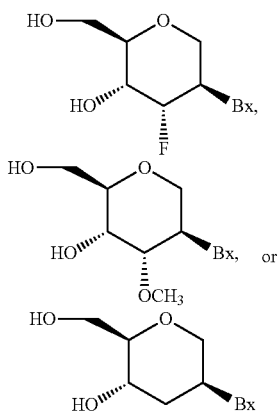

Many other bicyclo and tricyclo sugar surrogate ring systems are also known in the art that can be used to modify nucleosides for incorporation into antisense compounds (see for example review article: Leumann, J. C, Bioorganic & Medicinal Chemistry, 2002, 10, 841-854). Such ring systems can undergo various additional substitutions to enhance activity.

Methods for the preparations of modified sugars are well known to those skilled in the art. In nucleotides having modified sugar moieties, the nucleobase moieties (natural, modified or a combination thereof) are maintained for hybridization with an appropriate nucleic acid target.

In certain embodiments, antisense compounds targeted to a translation start site for expanded repeat (e.g., DPR) protein synthesis-containing nucleic acid comprise one or more kinds of modified nucleotides. In one embodiment, antisense compounds targeted to a translation start site for expanded repeat (e.g., DPR) protein synthesis-containing nucleic acid comprise 2'-modified nucleotides. In one embodiment, antisense compounds targeted to a translation start site for expanded repeat (e.g., DPR) protein synthesis-containing nucleic acid comprise a 2'-O-methyl RNA, a 2'-O-methoxyethyl RNA, or a 2'-fluoro RNA. In one embodiment, antisense compounds targeted to a translation start site for expanded repeat (e.g., DPR) protein synthesis-containing nucleic acid comprise tricyclo-DNA. Tricyclo-DNA belongs to a class of constrained DNA analogs that display improved hybridizing capacities to complementary RNA, see, e.g., Ittig et al., Nucleic Acids Res. 32:346-353 (2004); Ittig et al., Prague, Academy of Sciences of the Czech Republic. 7:21-26 (Coll. Symp. Series, Hocec, M., 2005); Ivanova et al., Oligonucleotides 17:54-65 (2007); Renneberg et al., Nucleic Acids Res. 30:2751-2757 (2002); Renneberg et al., Chembiochem. 5:1114-1118 (2004); and Renneberg et al., JACS. 124:5993-6002 (2002). In one embodiment, antisense compounds targeted to a translation start site for expanded repeat (e.g., DPR) protein synthesis-containing nucleic acid comprise a locked nucleotide, an ethyl-constrained nucleotide, or an alpha-L-locked nucleic acid. Various alpha-L-locked nucleic acids are known by those of ordinary skill in the art, and are described in, e.g., Sorensen et al., J. Am. Chem. Soc. (2002) 124(10):2164-2176.

In certain embodiments, antisense compounds targeted to a translation start site for expanded repeat (e.g., DPR) protein synthesis-containing nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format, wherein 9 non-locked nucleotides are flanked by 3 locked nucleotides on each side.

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to a translation start site for expanded repeat (e.g., DPR)

protein synthesis-containing nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format, wherein 9 non-locked nucleotides are flanked by 3 locked nucleotides on each side. In certain embodiments, antisense compounds targeted to a translation start site for expanded repeat (e.g., DPR) protein synthesis-containing nucleic acid comprise one or more modified nucleotides. In some embodiments, the modified nucleotide is 5-methylcytosine. In certain embodiments, each cytosine is a 5-methylcytosine.

In some embodiments, an antisense compound of the present disclosure directs translational inhibition of a translation start site for expanded repeat (e.g., DPR) protein synthesis-containing transcript by blocking translation initiation. In some embodiments the antisense compound is an RNase H-dependent antisense oligonucleotide. In some embodiments, an antisense oligonucleotide of the present disclosure is an RNase H-dependent antisense oligonucleotide, and may be a single-stranded, chemically modified oligonucleotide that binds to a complementary sequence in the target mRNA (e.g., a translation start site for expanded repeat (e.g., DPR) protein synthesis-containing mRNA). An RNase H-dependent antisense oligonucleotide of the present disclosure reduces expression of a target gene by RNase H-mediated cleavage of the target mRNA, and by inhibition of translation by steric blockade of ribosomes. In some embodiments, an antisense compound of the present disclosure is capable of mediating cleavage of at least 50%, at least 55%, at least 60%, at least 65%, at least 70%, at least 75%, at least 80%, at least 85%, at least 90%, at least 95% or more of a translation start site for expanded repeat (e.g., DPR) protein synthesis-containing transcripts by RNase-H. In one embodiment, the antisense compound is capable of mediating translational inhibition of at least 80% of a translation start site for expanded repeat (e.g., DPR) protein synthesis-containing transcripts. In one embodiment, the antisense compound is capable of mediating translational inhibition of at least 90% of a translation start site for expanded repeat (e.g., DPR) protein synthesis-containing transcripts.

In certain embodiments, an antisense compound that targets a translation start site for expanded repeat (e.g., DPR) protein synthesis-containing transcript is from about 6 to about 24 subunits in length. In other embodiments, the antisense compound that targets a translation start site for expanded repeat (e.g., DPR) protein synthesis-containing transcript is from about 8 to about 80 subunits in length. For example, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments, the antisense compounds are less than 40 linked subunits in length. In some embodiments, the antisense compounds are from about 12 to about 25 linked subunits in length. In some embodiments, the antisense compounds are from about 15 to about 20 linked subunits in length. In some embodiments, the antisense compound is an antisense oligonucleotide that targets a translation start site for expanded repeat (e.g., DPR) protein synthesis-containing transcript, and the linked subunits are linked nucleotides.

In certain embodiments antisense compounds targeted to a translation start site for expanded repeat (e.g., DPR) protein synthesis-containing transcript may be shortened or truncated. For example, a single subunit may be deleted from the 5' end (5' truncation), or alternatively from the 3' end (3' truncation). A shortened or truncated antisense compound targeted to a translation start site for expanded repeat (e.g., DPR) protein synthesis-containing transcript may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Branched Antisense Compounds

The present disclosure also provides branched antisense compounds comprising at two or more target-recognition sequences that targets a portion of a translation start site for expanded repeat (e.g., DPR) protein synthesis-containing nucleic acid. A branched antisense compound of the present disclosure may be, e.g., a branched antisense oligonucleotide compound.

As used herein, the term "branched antisense compound" or "branched antisense oligonucleotide" refers to two or more antisense compounds or antisense oligonucleotides are described herein, connected together.

In one embodiment, a branched oligonucleotide compound comprises two or more target-recognition sequences, wherein the target-recognition sequences are connected to one another by one or more moieties selected from a linker, a spacer, and a branching point. Target-recognition sequences are described herein. In some embodiments, the branched oligonucleotide compound comprises 2, 3, 4, 5, 6, 7, 8, or more target-recognition sequences, wherein each target-recognition sequence comprises a 5' end and a 3' end, and each target-recognition sequence is independently connected to a linker, a spacer, or a branching point at the 5' end or the 3' end. In some embodiments, each target-recognition sequence is connected to a linker, a spacer, or a branching point at the 5' end. In some embodiments, each target-recognition sequence is connected to a linker, a spacer, or a branching point at the 3' end. In another embodiment, each target-recognition sequence is connected to a linker, a spacer, or a branching point. In some embodiments, each of the target-recognition sequences are antisense compounds and/or oligonucleotides that target a portion of a translation start site for expanded repeat (e.g., DPR) protein synthesis-containing nucleic acid.

In some embodiments, a branched oligonucleotide compound of the present disclosure has the formula:

L-(N)$_n$ wherein N represents a target-recognition sequence of the present disclosure; n represents an integer, e.g., 2, 3, 4, 5, 6, 7, or 8; and L represents a linker selected from an ethylene glycol chain, an alkyl chain, a peptide, RNA, DNA, a phosphate, a phosphonate, a phosphoramidate, an ester, an amide, a triazole, and any combination thereof.

In some embodiments, a branched oligonucleotide compound of the present disclosure has the formula:

L-(N)$_n$ wherein the compound optionally further comprises one or more branching points B, and wherein the compound optionally further comprises one or more spacers S. In such embodiments, each of the one or more branching points B independently represents a polyvalent organic species or derivative thereof, and each of the one or more spacers S is independently selected from an ethylene glycol chain, an alkyl chain, a peptide, RNA, DNA, a phosphate, a phosphonate, a phosphoramidate, an ester, an amide, a triazole, and any combination thereof. For example, a branched oligonucleotide compound of the present disclosure having the formula L-(N)n has a structure, not to be limited in any fashion, e.g.,

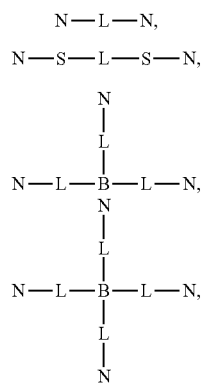

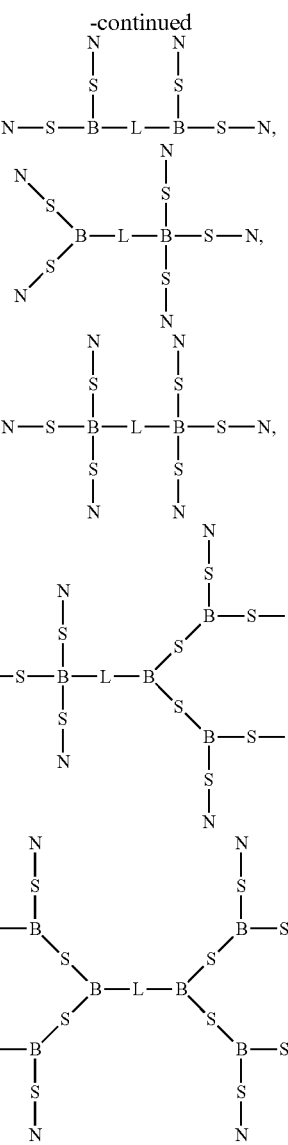

Conjugated Antisense Compounds

Antisense compounds may be covalently linked to one or more moieties or conjugates which enhance the activity, cellular distribution and/or cellular uptake of the resulting antisense oligonucleotides. Antisense compounds may be covalently linked to one or more moieties or conjugates which enhance and/or optimize pharmacokinetic parameters. Various pharmacokinetic parameters are known to a person of ordinary skill in the art, for example, absorbance, concentration of a compound in the body, the degree to which a compound permeates the body, the rate of elimination/clearance of a compound, the volume of plasma cleared of a compound per unit time, and others.

Typical conjugate groups include cholesterol moieties and lipid moieties. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). For example, a lipid moiety based on 1-O-hexa-decyloxy-1,3-propanediol can be conjugated to an antisense compound of the present disclosure. Such a lipid moiety has previously been shown to increase small molecule uptake and improve the oral bioavailability of nucleoside drugs (see, e.g., Aldern et al., Mol. Pharmacol. 2003, 63:678-681; and Hostetler, Antiviral Res. 2009, 82:A84-A98). Additional conjugate groups include carbohydrates, phospholipids, biotin, phenazine, folate, phenanthridine, anthraquinone, acridine, fluoresceins, rhodamines, coumarins, and dyes. In some embodiments, conjugation of a ligand to an antisense compound allows recognition by cell-surface receptors (see, e.g., Wolfrum et al., Nat. Biotechnol. 2007, 25:1149-1157; Hostetler et al., Antiviral Chem. Chemother. 2001, 12:61-70; and Prakash et al., Nucleic Acids Res. 2014, 42:8796-807). Methods of attaching one or more moieties or conjugates are well known in the art.

Antisense compounds can also be modified to have one or more stabilizing groups that are generally attached to one or both termini of the antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In some embodiments, an antisense compound of the present disclosure comprises a conjugate. In one embodiment, an antisense compound of the present disclosure comprises a target-recognition sequence and a conjugate, wherein the conjugate is linked to the target-recognition sequence. In some embodiments, the conjugate is selected from any of the conjugates described herein, for example, a hydrophobic conjugate, a tissue-targeting conjugate, or a conjugate designed to optimize pharmacokinetic parameters. A hydrophobic conjugate useful for conjugating to antisense compounds of the present disclosure, includes a hexadecyloxypropyl conjugate, a cholesterol conjugate, a polyunsaturated fatty acid conjugate, and others known in the art that may improve cellular uptake of a conjugate antisense compound. In some embodiments, the conjugate may be a tissue-targeting conjugate, for example, a carbohydrate conjugate, or a peptide conjugate, or any conjugate known in the art that can target an antisense compound of the present disclosure to a specific tissue. In some embodiments, an antisense compound of the present disclosure is conjugated with a polyethylene glycol conjugate. In one embodiment, a polyethylene glycol conjugate antisense compound optimizes pharmacokinetic properties of the antisense compound.

In some embodiments, the present disclosure provides a biostable antisense compound. In one embodiment, the biostable antisense compound comprises a target-recognition sequence and a conjugate, wherein the conjugate is linked to the target-recognition sequence. In some embodiments, the conjugate of a conjugated antisense compound remains stably linked to the antisense compound after cellular internalization. In one embodiment, the conjugate of a conjugate antisense compound remains stably linked to the target-recognition sequence after cellular internalization.

In some embodiments, the present disclosure provides biocleavable analogues of antisense oligonucleotides described herein. In such cases, biocleavable analogues comprise a hydrophobic conjugate that leads to stronger association with cell membranes and a linker. In one embodiment, the linker is a cleavable linker that when cleaved, releases the antisense oligonucleotide, e.g., releases the antisense oligonucleotide into endosomes. In some embodiments, an antisense compound comprises a cleavable linker, wherein the cleavable linker degrades when cleaved. In some embodiments, the linker is a nuclease-cleavable linker comprising a phosphodiester linkage. In some embodiments, the nuclease-cleavable linker comprising a phosphodiester linkage is about 2 to about 8 nucleotides. For example, a nuclease-cleavable phosphodiester linker can be 3, 4, 5, 6, 7, 8 nucleotides in length, or longer, e.g., 9, 10, 11, 12, 13, 14, 15, 16, 17, 18 nucleotides in length, or longer. In one embodiment, the nuclease-cleavable linker comprises about 6 nucleotides. In some embodiments, the cleavable linker is cleaved after cellular internalization. In some embodiments, the cleavable linker is cleaved within an endosome. In some embodiments, the cleavable linker is cleaved under reducing conditions. In some embodiments, the cleavable linker is cleaved under changing pH conditions, for example the cleavable linker is cleaved when the pH decreases, or when the pH increases. In some embodiments, the cleavable linker is cleaved by an intracellular nuclease or protease. In some embodiments, the cleavable linker is cleaved by an endosomal nuclease or protease.

Clustered Regularly Interspaced Short Palindromic Repeat (CRISPR)

Clustered regularly interspaced short palindromic repeat (CRISPR) RNA sequences and CRISPR-associated (Cas) genes generate catalytic protein-RNA complexes that utilize the incorporated RNA to generate sequence-specific double strand breaks at a complementary DNA sequence. Bhaya et al., (2011). The Cas9 nuclease from *Streptococcus pyogenes* (hereafter, Cas9) can be guided to specific sites in the human genome through base-pair complementation between a 20-nucleotide guide region of an engineered single-guide RNA (sgRNA) and a genomic target sequence. Mali et al., (2013b); Cho et al., (2013); Cong et al., (2013); and Jinek et al., (2013). A catalytically-inactive programmable RNA-dependent DNA-binding protein (dCas9) can be generated by mutating the endonuclease domains within Cas9 which can modulate transcription in bacteria or eukaryotes either directly or through an incorporated effector domain. Qi et al., (2013); Bikard et al., (2013); Gilbert et al., (2013a); Mali et al., (2013a); Konermann et al., (2013); Maeder et al., (2013); and Perez-Pinera et al., (2013).

CRISPR-based defense systems are found broadly in bacterial and archaeal systems. Type II systems employ a single protein, Cas9, to facilitate RNA-guided cleavage of a target DNA sequence complementary to the sgRNA and the protospacer adjacent motif (PAM) recognized by Cas9, where both elements must be recognized to achieve efficient DNA cleavage. Sorek, R. et al. (2013) "CRISPR-Mediated Adaptive Immune Systems in Bacteria and Archaea," Ann. Rev. Biochem. 82(1), 237-266; and Hsu, P. D. et al. (2013) "DNA targeting specificity of RNA-guided Cas9 nucleases," Nat. Biotechnol. 31(9), 827-832.

The Cas9 nuclease from S. pyogenes (hereafter, spCas9) can be targeted to a specific sequence through Watson-Crick pairing between a 20-nucleotide guide region of an engineered single-guide RNA (sgRNA) and a target sequence. The N. meningitidis Cas9 (nmCas9) recognizes a larger PAM element and employs a different (orthogonal) guide RNA. Hou, Z. et al. (2013) "Efficient genome engineering in human pluripotent stem cells using Cas9 from Neisseria meningitidis," P.N.A.S. 1 10(39), 15644-15649; and Zhang, Y. et al. (2013) "Processing-Independent CRISPR RNAs Limit Natural Transformation in Neisseria meningitidis," Mol. Cell 50(4), 488-503.

A catalytically-inactive programmable, RNA-dependent DNA-binding protein (the nuclease-dead versions of these Cas9 variants: dspCas9 or dnmCas9) can be generated by mutating the RuvC and HNH endonuclease domains within Cas9, which can modulate transcription in bacteria or eukaryotes either directly or through an incorporated effector domain.

Various systems involving CRISPR-Cas systems have been described. For example, a prokaryotic type II CRISPR-Cas system can be adapted to enable targeted genome modifications across a range of eukaryotes. Mali, P. et al. (2013). The reference describes an engineered system to enable RNA-guided genome regulation in human cells by tethering transcriptional activation domains either directly to a nuclease-null Cas9 protein or to an aptamer-modified single guide RNA (sgRNA). Using this functionality, a transcriptional activation-based assay was developed to determine the landscape of off-target binding of sgRNA:Cas9 complexes and compared it with the off-target activity of transcription activator like effectors (TALEs).

A CRISPR-associated catalytically inactive Cas9 protein (dCas9) has been described that offers a general platform for RNA-guided DNA targeting. Gilbert, et al. (2013). Here, the reference describes that fusion of dCas9 to effector domains with distinct regulatory functions enables stable and efficient transcriptional repression or activation in human and yeast cells, with the site of delivery determined solely by a co-expressed short guide (sg)RNA. The reference employs a lentiviral delivery system to introduce the elements into the cells.

A single or a plurality of sgRNAs can direct dCas9 fused to a VP64 transcriptional activation domain to increase expression of endogenous human genes targeting gene transcriptional activation and repression in human cell lines and activation in E. coli cells. The results suggest that multiple or a plurality of sgRNA-dCas9-VP64 complexes can function efficiently together in a single cell. Maeder, et al. (2013).

It has been described that the use of a Cas9 nuclease mutant that retains DNA-binding activity and can be engineered as a programmable transcription repressor by preventing the binding of the RNA polymerase (RNAP) to promoter sequences or as a transcription terminator by blocking the running RNAP in bacteria. In addition, a fusion between the omega subunit of the RNAP and a Cas9 nuclease mutant directed to bind upstream promoter regions can achieve programmable transcription activation. Bikard, et al. (2013).

A catalytically dead Cas9 lacking endonuclease activity has been reported that when co-expressed with a guide RNA, generates a DNA recognition complex that can specifically interfere with transcriptional elongation, RNA polymerase binding, or transcription factor binding. This system, which is referred to as CRISPR interference (CRISPRi), can efficiently repress expression of targeted genes in Escherichia coli, with no detectable off-target effects. Qi, et al. (2013).

A catalytically dead Cas9 with a fused activation domain has been reported that when co-expressed with a guide RNA, generates a DNA recognition complex that can specifically activate transcriptional elongation of genes, but that 3 to 4 sgRNAs are required for robust activity. This system, which is referred to as CRISPR-on, was used to activate genes in mouse embryonic stem cells (mESCs), HeLa cells and mouse zygotes. Cheng, A. W. et al. (2013) "Multiplexed activation of endogenous genes by CRISPR-on, an RNA-guided transcriptional activator system," Cell Res. 23(10), 1163-1171.

A CRISPR targeting process has been described that relies on CRISPR components; is sequence-specific; and, upon simultaneous introduction of a plurality of custom guide RNA (gRNAs), can effect multiplex editing of target loci. The reference describes engineering the type II bacterial CRISPR system to function with custom (sgRNA) in human cells. For the endogenous AAVS1 locus, targeting rates of 10 to 25% in 293T cells was obtained, 13 to 8% in K562 cells, and 2 to 4% in induced pluripotent stem cells. The reference describes the results as establishing an RNA-guided editing tool for facile, robust, and multiplexable human genome engineering. Mali, et al. (2013).

An approach that combines a Cas9 nickase mutant with paired guide RNAs to introduce targeted double-strand breaks has also been reported. Ran, F. A. et al. (2013) "Double Nicking by RNA-Guided CRISPR Cas9 for Enhanced Genome Editing Specificity," Cell 154(6), 1380-1389. Because individual nicks in the genome are repaired with high fidelity, simultaneous nicking via appropriately offset guide RNAs is required for double-stranded breaks and extends the number of specifically recognized bases for target cleavage. The reference describes that using paired nicking can reduce off-target activity by 50- to 1,500-fold in cell lines and to facilitate gene knockout in mouse zygotes without sacrificing on-target cleavage efficiency. The reference speculates that the versatile strategy enables a wide variety of genome editing applications that require high specificity.

The use of a CRISPR-Cas system from Neisseria meningitides has been reported to demonstrate efficient targeting of an endogenous gene in three hPSC lines using homology-directed repair (HDR). The Cas9 RNA-guided endonuclease from N. meningitidis (NmCas9) recognizes a 5'-NNNN-GATT-3' protospacer adjacent motif (PAM) different from those recognized by Cas9 proteins from S. pyogenes and S. thermophilus (SpCas9 and StCas9, respectively). Similar to SpCas9, NmCas9 is able to use a single-guide RNA (sgRNA) to direct its activity. Because of its distinct protospacer adjacent motif, the N. meningitidis CRISPR-Cas machinery increases the sequence contexts amenable to RNA-directed genome editing. Hou et al. (2013).

A "CRISPRi system" derived from the Streptococcus pyogenes CRISPR pathway has been reported that requires only the co-expression of a catalytically inactive Cas9 protein (lacking nuclease activity) and a customizable single guide RNA (sgRNA). The Cas9-sgRNA complex binds to DNA elements complementary to the sgRNA and causes a steric block that halts transcript elongation by RNA polymerase, resulting in the repression of the target gene. Larson, M. H. et al. (2013) "CRISPR interference (CRISPRi) for sequence-specific control of gene expression," Nat. Protoc. 8(11), 2180-2196.

Transcription Activator Like Effector Nucleases (TALENs)

Transcription Activator-Like Effector Nucleases (TALENs) are artificial restriction enzymes generated by fusing the TAL effector DNA binding domain to a DNA cleavage domain. These reagents enable efficient, programmable, and specific DNA cleavage and represent powerful tools for genome editing in situ. Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA. See U.S. Ser. No. 12/965,590; U.S. Ser. No. 13/426,991 (U.S. Pat. No. 8,450,471); U.S. Ser. No. 13/427,040 (U.S. Pat. No. 8,440,431); U.S. Ser. No. 13/427,137 (U.S. Pat. No. 8,440,432); and U.S. Ser. No. 13/738,381, and U.S. Pat. No. 9,393,257, all of which are incorporated by reference herein in their entirety.

TAL effectors are proteins secreted by *Xanthomonas* bacteria. The DNA binding domain contains a highly conserved 33-34 amino acid sequence with the exception of the 12th and 13th amino acids. These two locations are highly variable (Repeat Variable Di-residue (RVD)) and show a strong correlation with specific nucleotide recognition. This simple relationship between amino acid sequence and DNA recognition has allowed for the engineering of specific DNA binding domains by selecting a combination of repeat segments containing the appropriate RVDs.

The non-specific DNA cleavage domain from the end of the Fok1 endonuclease can be used to construct hybrid nucleases that are active in a yeast assay. These reagents are also active in plant cells and in animal cells. Initial TALEN studies used the wild-type Fok1 cleavage domain, but some subsequent TALEN studies also used Fok1 cleavage domain variants with mutations designed to improve cleavage specificity and cleavage activity. The Fok1 domain functions as a dimer, requiring two constructs with unique DNA binding domains for sites in the target genome with proper orientation and spacing. Both the number of amino acid residues between the TALEN DNA binding domain and the Fok1 cleavage domain and the number of bases between the two individual TALEN binding sites are parameters for achieving high levels of activity. The number of amino acid residues between the TALEN DNA binding domain and the Fok1 cleavage domain may be modified by introduction of a spacer (distinct from the spacer sequence) between the plurality of TAL effector repeat sequences and the Fok1 endonuclease domain. The spacer sequence may be 12 to 30 nucleotides.

The relationship between amino acid sequence and DNA recognition of the TALEN binding domain allows for designable proteins. In this case, artificial gene synthesis is problematic because of improper annealing of the repetitive sequence found in the TALE binding domain. One solution to this is to use a publicly available software program (DNAWorks) to calculate oligonucleotides suitable for assembly in a two-step PCR; oligonucleotide assembly followed by whole gene amplification. A number of modular assembly schemes for generating engineered TALE constructs have also been reported. Both methods offer a systematic approach to engineering DNA binding domains that is conceptually similar to the modular assembly method for generating zinc finger DNA recognition domains.

Once the TALEN genes have been assembled they are inserted into plasmids; the plasmids are then used to transfect the target cell where the gene products are expressed and enter the nucleus to access the genome. TALENs can be used to edit genomes by inducing double-strand breaks (DSB), which cells respond to with repair mechanisms. In this manner, they can be used to correct mutations in the genome which, for example, cause disease.

MegaTALs

MegaTALs are fusion proteins that combine homing endonucleases with modular DNA binding domains of TALENs, resulting in improved DNA sequence targeting and increased gene editing efficiencies. N-terminal fusions of TAL anchors can be employed to increase the specificity and activity of a gene-targeted endonuclease, including one or more homing endonucleases such as one or more of the I-HjeMI, I-CpaMI, and I-Onul homing endonucleases. MegaTALs can be constructed using the Golden Gate assembly strategy described by Cermak et al, Nucl. Acids Res. 39:e82-e82 (2011), using, e.g., an RVD plasmid library and destination vector.

Since megaTALs still cut DNA using homing endonuclease cleavage biochemistry, they engage DNA repair pathways in a manner distinct from all other gene editing nucleases. MegaTALs can be designed and predicted according to the procedures in WO 2013/126794 and WO 2014/191525 can be used in the present methods.

Meganucleases

A meganuclease refers to a double-stranded endonuclease having a polynucleotide recognition site of 14-40 base pairs, which can be either monomeric or dimeric. Meganucleases can be designed and predicted according to the procedures in US 2014/0121115 can be used in the present methods.

A "custom-made meganuclease" refers to a meganuclease derived from a parental meganuclease that possesses a recognition and/or cleavage that is altered from the parental meganuclease.

Exemplary meganucleases include, but are not limited to, I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-May I, PI-Mch I, PI-Mfu I, PI-Mfl I, PI-Mga I, PI-Mgo I, PI Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I; preferably, I-Sce I, I-Chu I, I-Dmo I, I-Cre I, I-Csm I, PI-Sce I, PI-Pfu I, PI-Tli I, PI-Mtu I, and I-Ceu I; more preferably, I-Dmo I, I-Cre I, PI-Sce I, and PI-Pfu I.

Zinc Finger Nucleases (ZFNs)

Zinc finger nucleases (ZFNs) are enzymes having a DNA cleavage domain and a DNA binding zinc finger domain. ZFNs may be made by fusing the nonspecific DNA cleavage domain of an endonuclease with site-specific DNA binding zinc finger domains. Such nucleases are powerful tools for gene editing and can be assembled to induce double strand breaks (DSBs) site-specifically into genomic DNA. ZFNs allow specific gene disruption as during DNA repair, the targeted genes can be disrupted via mutagenic non-homologous end joint (NHEJ) or modified via homologous recombination (HR) if a closely related DNA template is supplied.

Zinc finger proteins can be designed and predicted according to the procedures in WO 98/54311, U.S. Pat. Nos.

9,187,758, 9,206,404 and 8,771,985 can be used in the present methods. WO 98/54311 discloses technology which allows the design of zinc finger protein domains that bind specific nucleotide sequences that are unique to a target gene. It has been calculated that a sequence comprising 18 nucleotides is sufficient to specify a unique location in the genome of higher organisms. Typically, therefore, the zinc finger protein domains are hexadactyl, i.e., contain 6 zinc fingers, each with its specifically designed alpha helix for interaction with a particular triplet. However, in some instances, a shorter or longer nucleotide target sequence may be desirable. Thus, the zinc finger domains in the proteins may contain at least 3 fingers, or from 2-12 fingers, or 3-8 fingers, or 3-4 fingers, or 5-7 fingers, or even 6 fingers. In one aspect, the ZFP contains 3 zinc fingers; in another aspect, the ZFP contains 4 zinc fingers. Additional description on ZFNs and their design for genome editing may be found in US 20120329067A1, incorporated herein by reference.

Recombinant Adeno-Associated Viruses

In some aspects, isolated AAVs are provided. As used herein with respect to AAVs, the term "isolated" refers to an AAV that has been isolated from its natural environment (e.g., from a host cell, tissue, or subject) or artificially produced. Isolated AAVs may be produced using recombinant methods. Such AAVs are referred to herein as "recombinant AAVs." Recombinant AAVs (rAAVs) may have tissue-specific targeting capabilities, such that a transgene of the rAAV is delivered specifically to one or more predetermined tissue(s). The AAV capsid is an important element in determining these tissue-specific targeting capabilities. Thus, a rAAV having a capsid appropriate for the tissue being targeted can be selected. In some embodiments, the rAAV comprises a capsid protein having an amino acid sequence corresponding to any one of AAV1, AAV2, AAV3, AAV4, AAV5, AAV6, AAV7, AAV8, AAV9, AAV.Rh10, AAV11 and variants thereof. The recombinant AAVs typically harbor a recombinant nucleic acid as described herein.

Methods for obtaining recombinant AAVs having a desired capsid protein are well known in the art (See, for example, U.S. Patent Publication Number 2003/0138772, the contents of which are incorporated herein by reference in their entirety). AAV capsid proteins that may be used in the rAAVs described herein include, for example, those disclosed in G. Gao, et al., J. Virol, 78(12):6381-6388 (June 2004); G. Gao, et al, Proc Natl Acad Sci USA, 100(10): 6081-6086 (May 13, 2003); US 2003-0138772, US 2007/0036760, US 2009/0197338, and WO 2010/138263, the contents of which relating to AAVs capsid proteins and associated nucleotide and amino acid sequences are incorporated herein by reference. Typically, the methods involve culturing a host cell which contains a nucleic acid sequence encoding an AAV capsid protein or fragment thereof; a functional rep gene; a recombinant AAV vector composed of AAV inverted terminal repeats (ITRs) and a transgene; and sufficient helper functions to permit packaging of the recombinant AAV vector into the AAV capsid proteins.

Suitable AAVs that may be used in the methods provided herein are disclosed in U.S. 2013/0195801, and U.S. 2012/0137379. The contents of these publications are incorporated herein by reference for all purposes.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing an rAAV described herein may be delivered to the packaging host cell using any appropriate genetic element (vector). The selected genetic element may be delivered by any suitable method, including those described herein. The methods used to construct any embodiment described herein are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well-known and the selection of a suitable method is not a limitation on the present invention. See, e.g., K. Fisher et al, J. Virol., 70:520-532 (1993) and U.S. Pat. No. 5,478,745.

In some embodiments, recombinant AAVs may be produced using the triple transfection method (e.g., as described in detail in U.S. Pat. No. 6,001,650, the contents of which relating to the triple transfection method are incorporated herein by reference). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. In some embodiments, the AAV helper function vector supports efficient AAV vector production without generating any detectable wild-type AAV virions (e.g., AAV virions containing functional rep and cap genes). Non-limiting exemplary vectors suitable for use include, but are not limited to, pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, transfected host cells are provided. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

In some aspects, isolated cells are provided. As used herein with respect to cell, the term "isolated" refers to a cell that has been isolated from its natural environment (e.g., from a tissue or subject). As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

The foregoing methods for packaging recombinant vectors in desired AAV capsids to produce the rAAVs described herein are not meant to be limiting and other suitable methods will be apparent to the skilled artisan.

Recombinant AAV Vectors

The recombinant nucleic acids described herein may be recombinant AAV vectors. The recombinant AAV vector may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more inhibitory nucleic acids (e.g., miRNAs) comprising a nucleic acid that targets an endogenous mRNA of a subject. The transgene may also comprise a region encoding an exogenous mRNA that encodes a protein (e.g., a fluorescent protein).

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter.

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

The AAV sequences of the vector typically comprise the cis-acting 5' and 3' inverted terminal repeat sequences (See, e.g., B. J. Carter, in "Handbook of Parvoviruses," ed., P. Tijsser, CRC Press, pp. 155 168 (1990)). The ITR sequences are about 145 bp in length. In some embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual," 2d ed., Cold Spring Harbor Laboratory, New York (1989); and K. Fisher et al., J Virol., 70:520 532 (1996)). An example of such a molecule employed as described herein is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

Thus, the recombinant nucleic acids may comprise inverted terminal repeats (ITR) of an AAV serotypes selected from the group consisting of: AAV1, AAV2, AAV5, AAV6, AAV6.2, AAV7, AAV8, AAV9, AAV.Rh10, AAV11 and variants thereof. The recombinant nucleic acids may also include a promoter operably linked with the one or more first inhibitory RNAs, the exogenous mRNA, and/or the one or more second inhibitory RNAs. The promoter may be tissue-specific promoter, a constitutive promoter or inducible promoter.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced as described herein. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly, two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., miRNA).

For nucleic acids encoding proteins, a polyadenylation sequence generally is inserted following the transgene sequences and before the 3' AAV ITR sequence. An exemplary rAAV construct may also contain an intron, desirably located between the promoter/enhancer sequence and the transgene. One possible intron sequence is derived from SV-40, and is referred to as the SV-40 T intron sequence. Any intron may be from the R-Actin gene. Another vector element that may be used is an internal ribosome entry site (IRES).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors described herein may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, and the dihydrofolate reductase promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system, the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In another embodiment, the native promoter, or fragment thereof, for the transgene will be used. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the promoter is a chicken R-actin promoter.

In some embodiments, one or more bindings sites for one or more of miRNAs are incorporated in a transgene of a rAAV vector, to inhibit the expression of the transgene in one or more tissues of a subject harboring the transgenes, e.g., non-liver tissues, non-lung tissues. The skilled artisan will appreciate that binding sites may be selected to control the expression of a transgene in a tissue specific manner. The miRNA target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

In some embodiments, the cloning capacity of the recombinant RNA vector may be limited and a desired coding sequence may involve the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Recombinant AAV Administration rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected tissue (e.g., liver tissue, lung tissue) and administration subcutaneously, intraopancreatically, intranasally, parenterally, intravenously, intramuscularly, intrathecally, intracerebrally, orally, intraperitoneally, by inhalation or by another route. Routes of administration may be combined, if desired.

Delivery of certain rAAVs to a subject may be, for example, by administration into the bloodstream of the subject. Administration into the bloodstream may be by injection into a vein, an artery, or any other vascular conduit. Moreover, in certain instances, it may be desirable to deliver the rAAVs to brain tissue, meninges, neuronal cells, glial cells, astrocytes, oligodendrocytes, cereobrospinal fluid (CSF), interstitial spaces and the like. In some embodiments, recombinant AAVs may be delivered directly to the spinal cord or brain (e.g., prefrontal cortex) by injection into the ventricular region, as well as to the striatum (e.g., the caudate nucleus or putamen of the striatum), and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

In certain circumstances it will be desirable to deliver the rAAV-based therapeutic constructs in suitably formulated pharmaceutical compositions disclosed herein either intrathecally, intracerebrally, intravenously, subcutaneously, intraopancreatically, intranasally, parenterally, intravenously, intramuscularly, orally, intraperitoneally, or by inhalation.

It can be appreciated by one skilled in the art that desirable administration of rAAV-based therapeutic constructs can also include ex vivo administration. In some embodiments, ex vivo administration comprises (1) isolation of cells or tissue(s) of interest from a subject, (2) contacting the cells or tissue(s) with rAAVs in sufficient amounts to transfect the cells or tissue to provide sufficient levels of gene transfer and expression without undue adverse effect, and (3) transferring cells or tissue back into the subject. In some embodiments, cells or tissues may be cultured ex vivo for several days before and/or after transfection.

Cells or tissues can be isolated from a subject by any suitable method. For example, cells or tissues may be isolated by surgery, biopsy (e.g., biopsy of skin tissue, lung tissue, liver tissue, adipose tissue), or collection of biological fluids such as blood. In some embodiments, cells are isolated from bone marrow. In some embodiments, cells are isolated from adipose tissue. In some embodiments, cells are isolated from a lipoaspirate. Appropriate methods for isolating cells from adipose tissue for ex vivo transfection are known in the art. See, e.g., Kuroda, M., et al., (2011), Journal of Diabetes Investigation, 2: 333-340; Kouki Morizono, et al. Human Gene Therapy. January 2003, 14(1): 59-66; and Patricia A. Zuk, Viral Transduction of Adipose-Derived Stem Cells, Methods in Molecular Biology, 1, Volume 702, Adipose-Derived Stem Cells, Part 4, Pages 345-357.

In some embodiments, the isolated cells comprise stem cells, pluripotent stem cells, neuroprogenitor cells, lipoaspirate derived stem cells, liver cells (e.g., hepatocytes), hematopoietic stem cells, mesenchymal stem cells, stromal cells, hematopoietic cells, blood cells, fibroblasts, endothelial cells, epithelial cells, or other suitable cells. In some embodiments, cells to be transfected are induced pluripotent stem cells prepared from cells isolated from the subject.

In an embodiment, cells or tissue(s) are transduced at a multiplicity of infection (MOI) of at least 10 infectious units (i.u.) of a rAAV per cell (for example, 10, 100, 1,000, 5,000, 10,000, 100,000 or more i.u.) or at a functionally equivalent viral copy number. In one embodiment, cells or tissue(s) are transduced at a MOI of 10 to 10,000 i.u. Routes for transfer of transfected cells or tissue(s) into a subject include, but are not limited to, subcutaneously, intraopancreatically, intranasally, parenterally, intravenously, intravascularly, intramuscularly, intrathecally, intracerebrally, intraperitoneally, or by inhalation. In some embodiments, transfected cells are administered by hepatic portal vein injection. In some embodiments, transfected cells are administered intravascularly. Methods for ex vivo administration of rAAV are well known in the art (see, e.g., Naldini, L. Nature Reviews Genetics (2011) 12, 301-315, Li, H. et al. Molecular Therapy (2010) 18, 1553-1558, and Loiler et al. Gene Therapy (2003) 10, 1551-1558).

Recombinant AAV Compositions

The rAAVs may be delivered to a subject in compositions according to any appropriate methods known in the art. The rAAV, which may be suspended in a physiologically compatible carrier (e.g., in a composition), may be administered to a subject, e.g., a human, mouse, rat, cat, dog, sheep, rabbit, horse, cow, goat, pig, guinea pig, hamster, chicken, turkey, or a non-human primate (e.g., Marmoset, Macaque). The compositions described herein may comprise a rAAV alone, or in combination with one or more other viruses (e.g., a second rAAV encoding having one or more different transgenes).

In some embodiments, to assess gene silencing in relatively large primates, experiments are performed in African Green Monkeys or other relatively large primates. In some embodiments, rAAV vectors expressing miRNAs (e.g., miR-C9ORF72 or miR-FMR1) are injected in the CSF of such primates both caudally using an IT injection and rostrally using cisterna *magna* injections.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. Still others will be apparent to the skilled artisan.

Optionally, compositions described herein may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The dose of rAAV virions required to achieve a desired effect or "therapeutic effect," e.g., the units of dose in vector genomes/per kilogram of body weight (vg/kg), will vary based on several factors including, but not limited to: the route of rAAV administration, the level of gene or RNA expression required to achieve a therapeutic effect, the specific disease or disorder being treated, and the stability of the gene or RNA product. One of skill in the art can readily determine a rAAV virion dose range to treat a subject having a particular disease or disorder based on the aforementioned factors, as well as other factors that are well known in the art. An effective amount of the rAAV is generally in the range of from about 10 µl to about 100 ml of solution containing from about $10^9$ to $10^{16}$ genome copies per subject. Other volumes of solution may be used. The volume used will typically depend, among other things, on the size of the subject, the dose of the rAAV, and the route of administration. For example, for intravenous administration a volume in range of 10 µl to 100 µl, 100 µl to 1 ml, 1 ml to 10 ml, or more may be used. In some cases, a dosage between about $10^{10}$ to $10^{12}$ rAAV genome copies per subject is appropriate. In some embodiments the rAAV is administered at a dose of $10^{10}$, $10^{11}$, $10^{12}$, $10^{13}$, $10^{14}$, or 105 genome copies per subject. In some embodiments the rAAV is administered at a dose of $10^{10}$, $10^{11}$, $10^{12}$, $10^{13}$, or $10^{14}$ genome copies per kg.

In some embodiments, rAAV compositions are formulated to reduce aggregation of AAV particles in the composition, particularly where high rAAV concentrations are present (e.g., about $10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Methods of Treatment

The present disclosure a method of treating a subject having a translation start site for expanded repeat (e.g., DPR) protein synthesis associated disease or disorder. Methods of treatment include administering to the subject in need thereof an effective amount of a translation modulating agent described herein. Such translation modulating agents include antisense oligonucleotides, a small interfering RNA (siRNAs), guide RNAs, zinc finger nucleases (ZFN), a transcription-activator like effector nucleases (TALEN), and RNA-guided nucleases (e.g., CRISPR/Cas9). The translation modulating agents described herein are designed to inhibit translation initiation from a translation start site for expanded repeat (e.g., DPR) protein synthesis identified herein. Such a translation start site for expanded repeat (e.g., DPR) protein synthesis includes those identified in the C9ORF72 and FMR1 mRNAs. Examples of a translation start site for expanded repeat (e.g., DPR) protein synthesis associated diseases or disorders, includes those diseases and disorders associated with the expression of dipeptide repeat (e.g., DPR) proteins.

Examples of translation start sites for expanded repeat (e.g., DPR) protein synthesis-associated diseases or disorders includes, without limitation, e.g., ALS, FTD, Huntington's disease, spinocerebellar ataxia type 3, spinocerebellar ataxia type 8, myotonic dystrophy type 1, and/or fragile X tremor/ataxia syndrome.

Pharmaceutical Compositions and Formulations

Provided herein are pharmaceutical compositions and formulations which include the translation start site for expanded repeat (e.g., DPR) protein synthesis inhibitor compositions described herein. Exemplary translation start site for expanded repeat (e.g., DPR) protein synthesis inhibitor compositions include, but are not limited to, antisense oligonucleotides, RNAi agents (such as siRNAs, miRNAs, and shRNAs), and genome-editing nucleases, such as clustered regularly interspaced short palindromic repeats (CRISPR)/Cas9 and their corresponding guide RNAs (gRNAs), transcription activator-like effector nucleases (TALENs), or zinc finger nucleases (ZFNs). For example, the translation start site for expanded repeat (e.g., DPR) protein synthesis inhibitor compositions described herein can be admixed, encapsulated, conjugated or otherwise associated with other molecules, molecule structures or mixtures of compounds. A pharmaceutical composition described herein is formulated to be compatible with its intended route of administration. Examples of routes of administration include oral administration, mucosal administration, subcutaneous administration, intramuscular administration, topical administration, intravenous administration, intrathecal administration, intracerebroventricular administration, or inhalation. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELm (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The pharmaceutical compositions can be administered in a number of ways depending on, for example, whether local or systemic treatment is desired and/or the area to be treated. In one embodiment, administration is topical to the surface of the respiratory tract, particularly nasal and pulmonary, e.g., by nebulization, inhalation, or insufflation of powders, solutions, gels, or aerosols (e.g., drops or sprays), by mouth and/or nose. For example, in some embodiments, a once-daily inhaler or a once-weekly nebulized formulation can be used. For administration by inhalation, the compounds are delivered in the form of an aerosol spray from pressured container or dispenser which contains a suitable propellant, e.g., a gas such as carbon dioxide, or a nebulizer.

The pharmaceutical compositions and formulations provided herein can, in some embodiments, be conveniently presented in unit dosage form and can be prepared according to conventional techniques well known in the pharmaceutical industry. Such techniques can include bringing into association the active ingredients with the pharmaceutical carrier(s) or excipient(s). In general, the formulations can be prepared by uniformly and intimately bringing into association the active ingredients with liquid carriers, finely divided solid carriers, or both, and then, if necessary, shaping the product (e.g., into a specific particle size for delivery). In one embodiment, the pharmaceutical formulations are prepared for pulmonary administration in an appropriate solvent, e.g., water or normal saline, and optionally in a sterile formulation with carriers or other agents to allow for the formation of droplets of the desired diameter for delivery using inhalers, nasal delivery devices, nebulizers, and other devices for pulmonary delivery. Alternatively, the pharmaceutical formulations can be formulated as dry powders for use in dry powder inhalers.

In some embodiments of the compositions (e.g., pharmaceutical compositions or formulations) provided herein, the translation start site for expanded repeat (e.g., DPR) protein synthesis inhibitor composition is formulated to be administered by systemic administration. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In other embodiments, the translation start site for expanded repeat (e.g., DPR) protein synthesis inhibitor composition is formulated to be administered by local administration. In some embodiments, the synthetic antisense oligonucleotide is formulated to be administered by intranasal, intratracheal, sublingual, aerosol and/or respiratory administration. In other embodiments, the translation start site for expanded repeat (e.g., DPR) protein synthesis inhibitor composition is administered by insufflation or as a nasal spray or nasal gel. In other embodiments, the synthetic antisense oligonucleotide is formulated to be administered using a nebulizer, nasal inhaler, metered dose inhaler, dry powder inhaler, pulmonary inhaler, or a combination thereof.

The compounds can also be prepared in the form of suppositories (e.g., with conventional suppository bases such as cocoa butter and other glycerides) or retention enemas for rectal delivery.

A translation start site for expanded repeat (e.g., DPR) protein synthesis inhibitor composition of the present disclosure, e.g., an antisense compound, RNAi agent, or genome-editing nuclease targeting a translation start site for expanded repeat (e.g., DPR) protein synthesis-containing nucleic acid can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

A translation start site for expanded repeat (e.g., DPR) protein synthesis inhibitor composition of the present disclosure, e.g., an antisense compound, RNAi agent, or genome-editing nuclease targeting a translation start site for expanded repeat (e.g., DPR) protein synthesis-containing nucleic acid can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms described herein are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in a method described herein, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

A translation start site for expanded repeat (e.g., DPR) protein synthesis inhibitor composition can be utilized in pharmaceutical compositions by combining the translation start site for expanded repeat (e.g., DPR) protein synthesis inhibitor composition with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising a translation start site for expanded repeat (e.g., DPR) protein synthesis inhibitor composition targeted to a translation start site for expanded repeat (e.g., DPR) protein synthesis-containing nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising inhibitor compositions including a translation start site for expanded repeat (e.g., DPR) protein synthesis encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of a translation start site for expanded repeat (e.g., DPR) protein synthesis inhibitor compositions, prodrugs, pharmaceutically acceptable salts of such prodrugs, and other bioequivalents. Suitable pharmaceutically acceptable salts include, but are not limited to, sodium and potassium salts.

Delivery vehicles such as liposomes, nanocapsules, microparticles, microspheres, lipid particles, vesicles, and the like, may be used for the introduction of compositions described herein into suitable host cells. In particular, the translation start site for expanded repeat (e.g., DPR) protein synthesis inhibitor compositions may be formulated for delivery either encapsulated in a lipid particle, a liposome, a vesicle, a nanosphere, or a nanoparticle or the like.

The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1—Mapping Translation Initiation Start Sites For Repeat Expansions

Translation initiation start sites were mapped for repeat expansion-containing mRNAs by performing ribosomal profiling. Induced pluripotent stem cell (iPSC) lines derived from three different patients with C9ORF72 repeat expansions, as well as iPSC lines derived from normal individuals were cultured in one of three reagents: i) cycloheximide, which freezes ribosomes on mRNA, ii) harringtonine, which freezes only the initiating ribosome on the translation start site while allowing the elongating ribosomes to run-off the mRNA, iii) lactimidomycin, which, like harringtonine, freezes only the initiating ribosome on the translation start site while allowing the elongating ribosomes to run-off the mRNA (FIG. 3-6).

After treatment with one of the three reagents, the iPSC cells were collected and RNA-seq and ribosome profiling libraries were prepared following established ribosomal profiling protocols. (See, Ingolia et al. 2009. Science 324:218; Ingolia et al. 2011. Cell 147:789; Lee et al. 2012. PNAS 109:E2424.)

Figure 7:
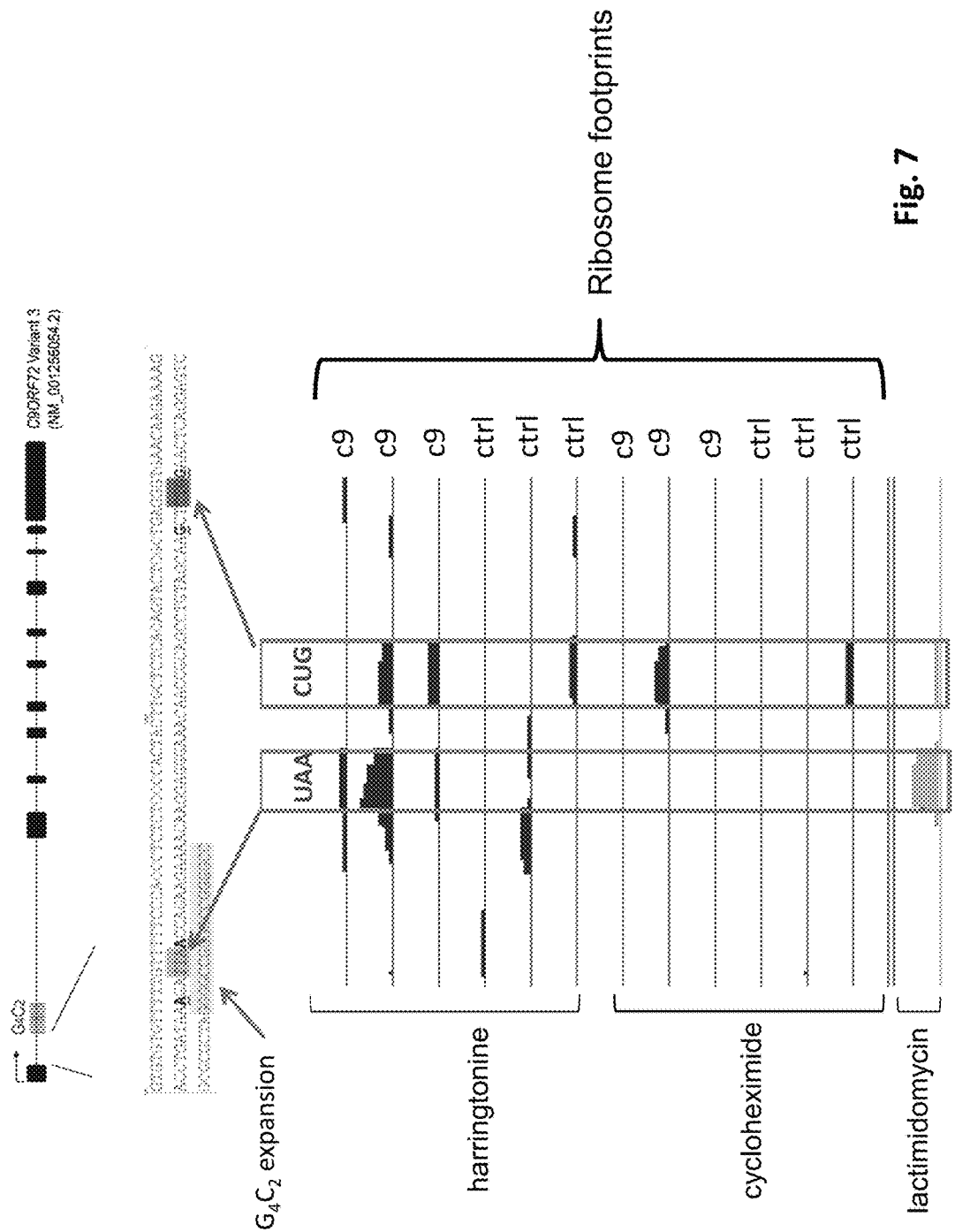
FIG. 7 depicts the results of the ribosomal profiling of C9ORF72 mRNA. Two novel translation start sites are shown relative to the surrounding nucleotide sequence of intron 1 of the C9ORF72 mRNA.
Figure 8B:
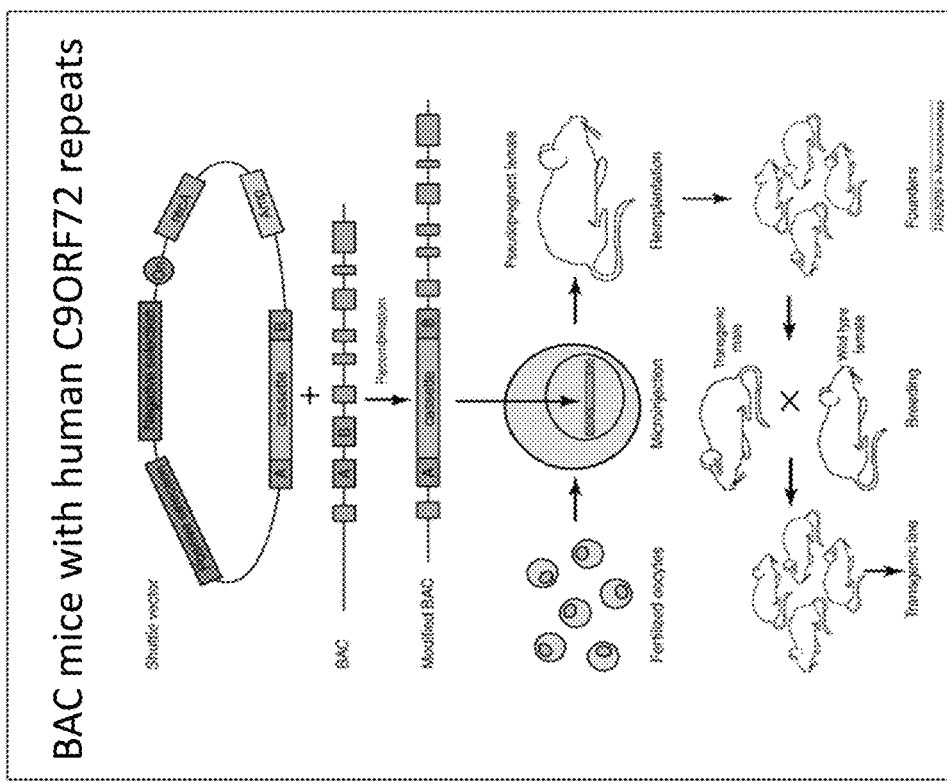
FIG. 8A-FIG. 8B schematically depict two studies according to particular embodiments.
Figure 8A:
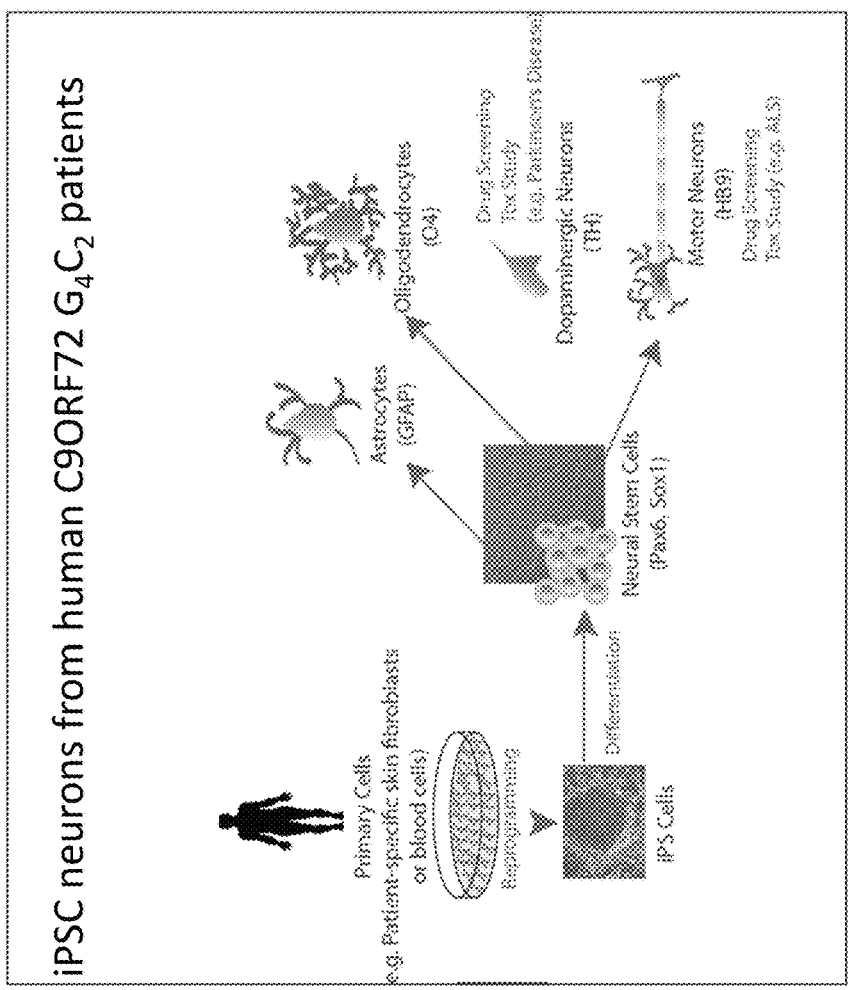

Analysis of RNA-seq and ribosomal profiling libraries revealed that there are two novel translation initiation sites for the C9ORF72 repeat expansion in intron 1. The first is UAA and the second is CUG (FIG. 7).

Example 2—Inhibition of C9ORF72-Related Toxic DPR Protein Synthesis

Inhibition of C9ORF72-related toxic DPR protein synthesis was achieved by using the CRISPR-Cas9 system on isogenic C9 iPSC lines containing a GGGGCC nucleotide repeat region of approximately 1,000 GGGGCC repeats. The CRISPR-Cas9 system was transfected into the C9 patient iPSC line along with guide RNAs that either flank the entire GGGGCC nucleotide repeat region or flank 86 nucleotides 5' of the GGGGCC nucleotide repeat region. Table 2 below recites the guide RNAs used to remove the 86 nucleotides 5' of the GGGGCC nucleotide repeat region as well as the 86-nucleotide sequence that was removed.

TABLE 2

Guide RNA sequences used to remove the 86 nucleotides 5' of the GGGCC nucleotide repeat region.

| SEQ ID NO | Sequence |
| --- | --- |
| SEQ ID NO: 4<br>Guide RNA 1 | GCTCTCACAGTACTCGCTGA |
| SEQ ID NO: 5<br>Guide RNA 2 | TGTAGCAAGCTCTGGAACTC |
| SEQ ID NO: 6<br>Excised region<br>of C9ORF72<br>gene | TGAGGGTGAACAAGAAAAGACCTGATAAAGATTAA<br>CCAGAAGAAAACAAGGAGGGAAACAACCGCAGC<br>CTGTAGCAAGCTCTGGAA |

Figure 9B:
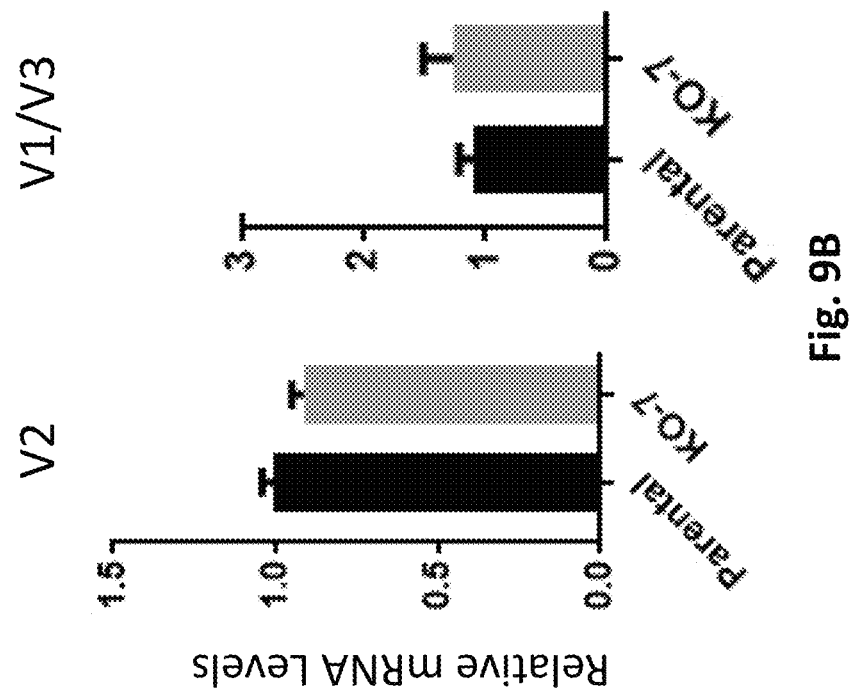
FIG. 9A-FIG. 9B depicts results derived from isogenic C9ORF72 iPSC lines generated by CRISPR.
Figure 9A:
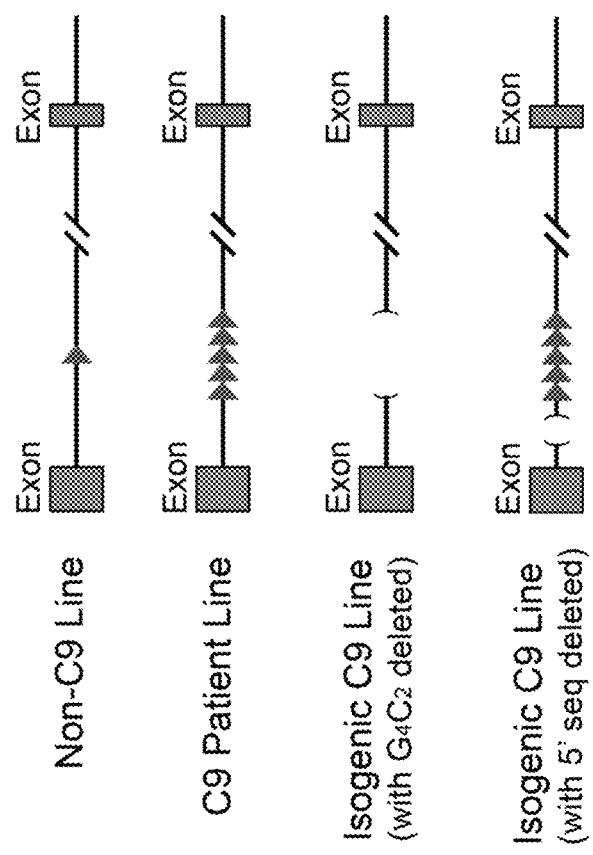
Figure 10:
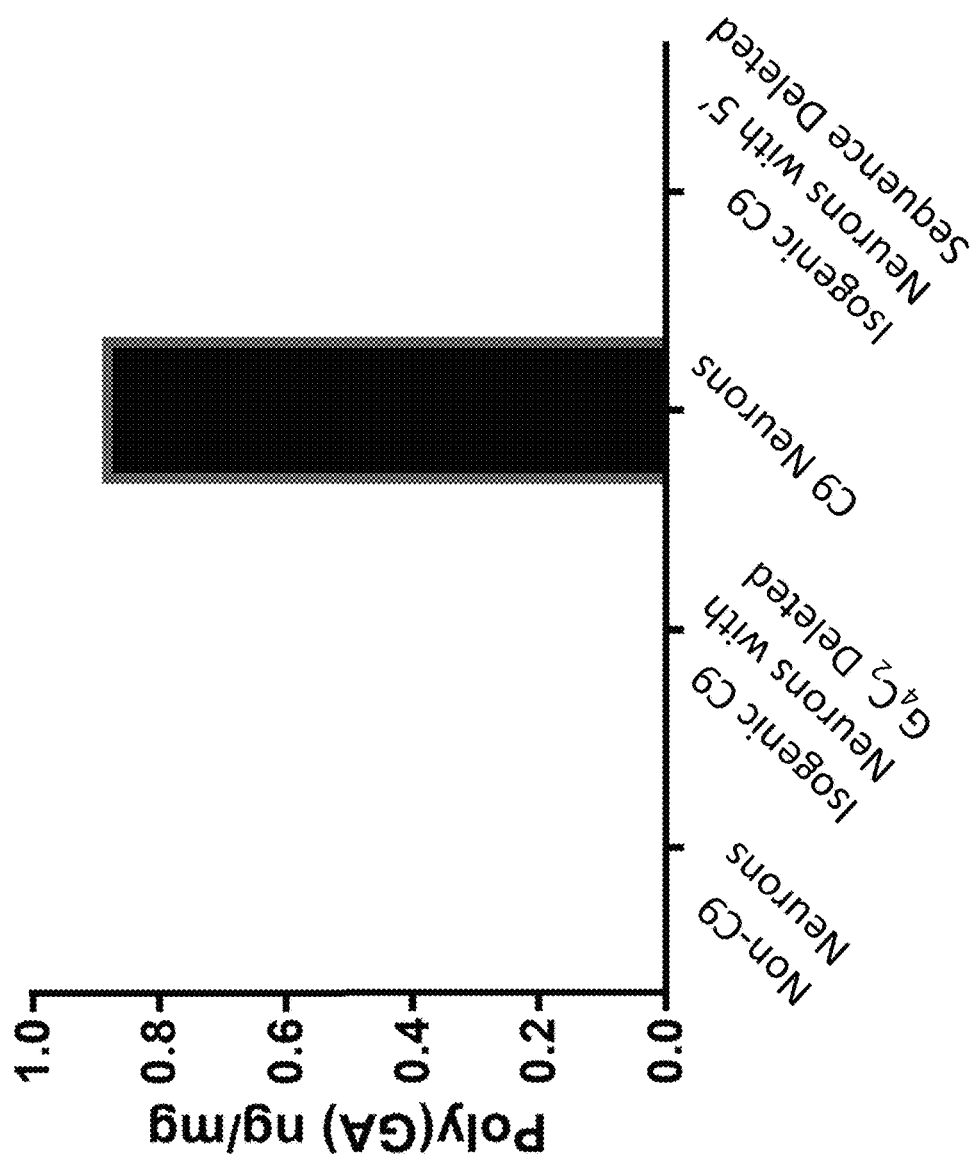
FIG. 10 depicts the levels of Poly(GA) peptide production in cells with a GGGGCC repeat in the C9ORF72 gene compared to cells which are derived from a control subject without expanded GGGGCC repeats and cells which have the repeat removed or the 86 nucleotides 5' to the GGGGCC repeat region removed.
Figure 11:
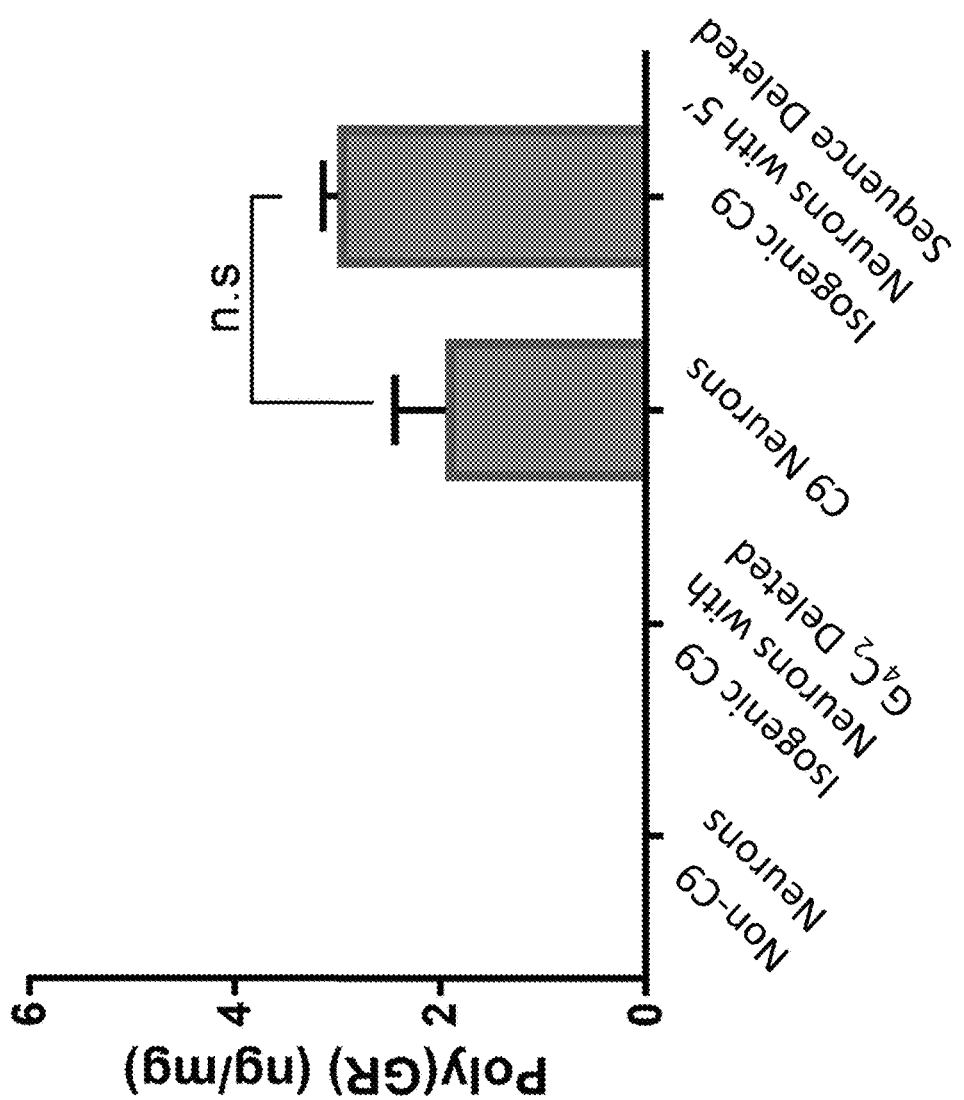
FIG. 11 depicts the levels of Poly(GR) peptide production in cells with a GGGGCC repeat in the C9ORF72 gene compared to cells which are derived from a control subject without expanded GGGGCC repeats and cells which have the repeat removed or the 86 nucleotides 5' to the GGGGCC repeat region removed.

As depicted in FIG. 9, removal of the 5' sequence does not affect expression of the C9ORF72 transcripts, V1, C2, and V3. Upon confirmation that C9ORF72 was still expressed, the levels of DPR proteins, Poly(GA) and Poly(GR) were determined using an ELISA-based assay for each peptide. As depicted in FIG. 10, Poly(GA) expression was eliminated in the isogenic C9 iPSC-derived neurons with either the entire GGGGCC repeat region removed or the 86 nucleotides 5' of the GGGGCC nucleotide repeat region removed. As depicted in FIG. 11, Poly(GR) expression was eliminated in the isogenic C9 iPSC-derived neurons with the entire GGGGCC repeat region removed but not in the isogenic C9 iPSC-derived neurons with the 86 nucleotides 5' of the GGGGCC nucleotide repeat region removed. It is hypothesized that ribosomes select a new translation start codon in iPSC line KO-7 to initiate poly(GR) production.

Figure 12:
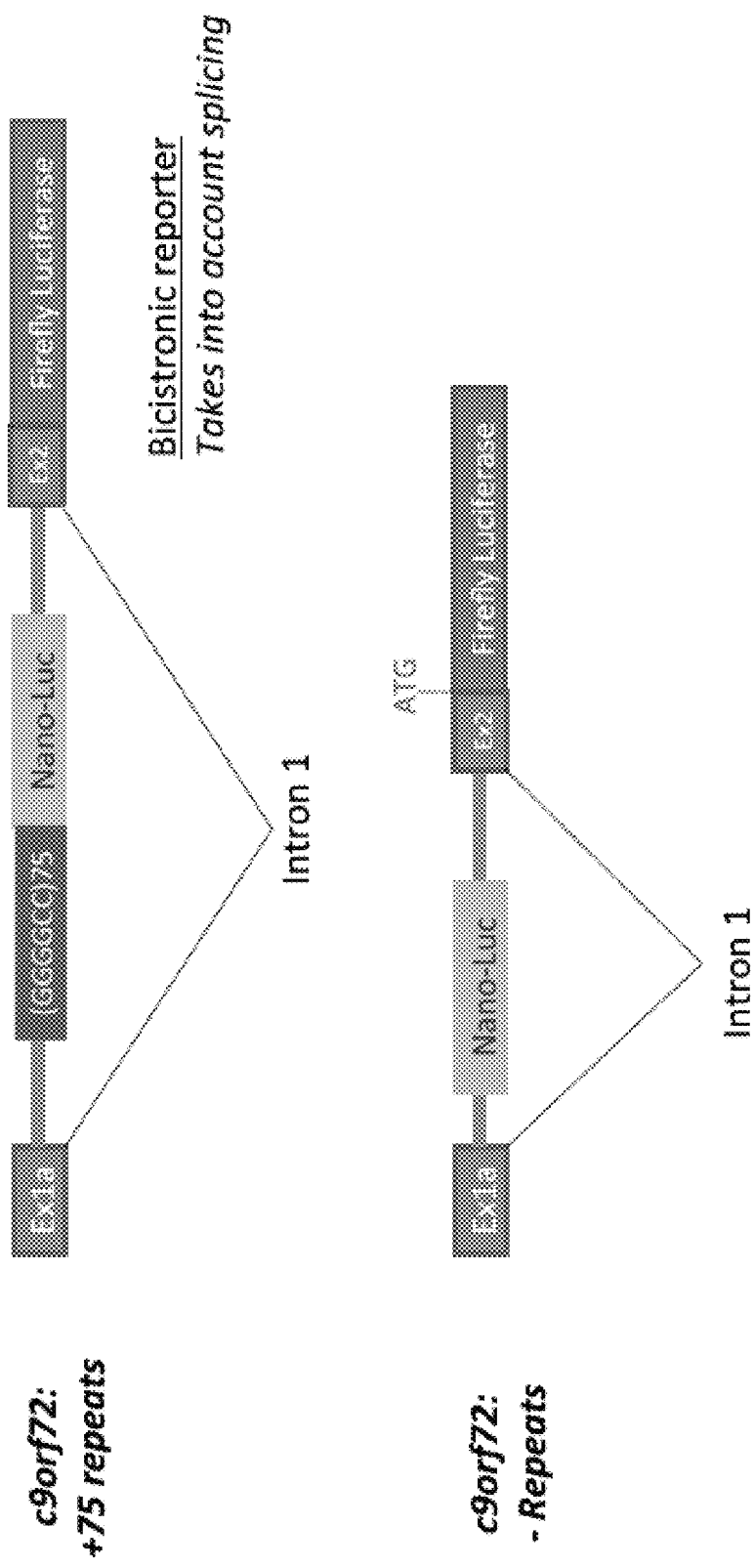
FIG. 12 depicts a schematic of the reporter assay-based method of mapping translation initiation start sites for repeat expansion regions.

Example 3—Reporter Assay for Mapping Translation Initiation Start Sites for Repeat Expansions A reporter assay-based method of mapping translation initiation start sites for repeat expansion regions similar to Example 1 above was developed. The reporter vector contains exon 1a, intron 1, and exon 2 of the C9ORF72 gene. Intron 1 in the reporter also contains a GGGGCC nucleotide repeat, as depicted in FIG. 12. The reporter vector is described in Cheng et al. 2018. Nat. Commun. 9(1): 51. Briefly, HEK293T cells were transfected using lipofectamine and collected 22 hours after transfection. After collection, ribosomal profiling was performed as described in Example 1.

Figure 13:
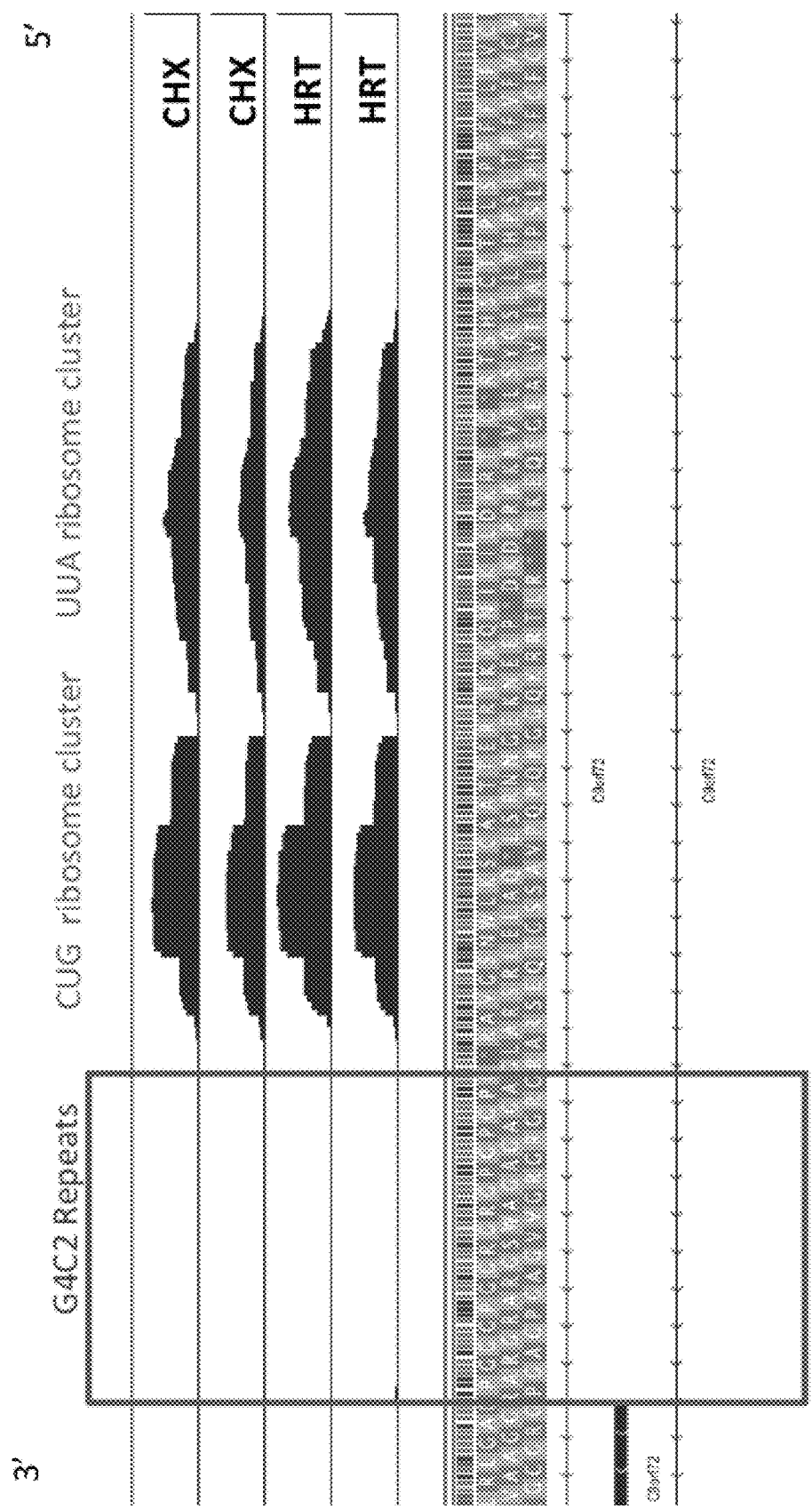
FIG. 13 depicts the results of the reporter assay-based method of mapping translation initiation start sites for repeat expansion regions following ribosomal profiling. The CUG and UUA translation initiation start sites were identified.

The results of the reporter assay-based method of mapping translation initiation start sites for repeat expansion regions yielded results similar to Example 1 above. The reporter assay performed better than the assay of Example 1 by yielding a better detection signal. As can be seen in FIG. 13, the same two novel translation initiation sites for the C9ORF72 repeat expansion in intron 1, CUG and UUA, were detected with this method.

Example 4—Additional Methods of Inhibiting C9ORF72-Related Toxic DPR Protein Synthesis Inhibition of C9ORF72-related toxic DPR protein synthesis may be achieved by any mechanism known in the art that is capable of disrupting a translation start site, whether at the genomic or transcript level.

Exemplary disruption methods include polypeptides that bind the gene at or near the site that encodes the translation start site one wishes to disrupt, or polypeptides that bind at or near the translation start site of the mRNA one wishes to disrupt. Examples of such polypeptides include zinc finger nucleases (ZFN), transcription-activator like effector nucleases (TALEN), and RNA-guided nucleases (e.g., Cas9 or Cpf1).

Additional exemplary disruption methods include nucleic acids that are sufficiently complementary to the gene at or near the site that encodes the translation start site one wishes to disrupt, or nucleic acids that are sufficiently complementary to a region at or near the translation start site of the mRNA one wishes to disrupt. Examples of such nucleic acids include antisense oligonucleotides (ASO), small interfering RNAs (siRNA), and guide RNAs (gRNA) that associate with CRISPR gene editing systems.

A particularly exemplary method will be to use antisense oligonucleotides which are sufficiently complementary to one or both of the novel translation start sites identified herein.

Example 5—Mapping Translation Initiation Start Sites for the FMR1 Transcript Repeat Region Translation initiation start sites for the repeat expansion region of the FMR1 transcript are mapped by performing ribosomal profiling. Cell lines harboring the FMR1 repeat expansion, as well as control cells with the repeat will be cultured in one of three reagents: i) cycloheximide; ii) harringtonine; or iii) lactimidomycin.

After treatment with one of the three reagents, the cells are collected and RNA-seq and ribosome profiling libraries are prepared following established ribosomal profiling protocols. (See, Ingolia et al. 2009. Science 324:218; Ingolia et al. 2011. Cell 147:789; Lee et al. 2012. PNAS 109:E2424.)

Analysis of RNA-seq and ribosomal profiling libraries should reveal novel translation initiation sites for the FMR1 repeat expansion.

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A translation modulating agent comprising a antisense oligonucleotide (ASO) that is sufficiently complementary to one or both translation initiation start codons UUA or CUG in a region of intron 1 of C9ORF72 (SEQ ID NO:1) to disrupt translation initiation at or near a translation start site for expanded repeat protein synthesis of an C9ORF72 mRNA, and thereby modulate expression of the mRNA.

2. The translation modulating agent of claim 1, wherein the translation start site for expanded repeat protein synthesis is upstream of a GGGGCC repeat expansion region in the C9ORF72 mRNA.

3. The translation modulating agent of claim 1, wherein the ASO is sufficiently complementary to SEQ ID NO: 2 to block translation initiation from TTA of SEQ ID NO:2.

4. The translation modulating agent of claim 1, wherein the ASO is sufficiently complementary to SEQ ID NO: 3 to block translation initiation from CTG of SEQ ID NO:3.

5. The translation modulating agent of claim 1, wherein the C9ORF72 mRNA is C9ORF72 variant 3, designated as NM_001256054.2.

6. The translation modulating agent of claim 1, wherein the agent prevents ribosome binding to the C9ORF72 mRNA.

7. The translation modulating agent of claim 1, wherein the agent inhibits translation of a C9ORF72 GGGGCC repeat expansion.

8. The translation modulating agent of claim 1, wherein the ASO comprises one or more modifications selected from the group consisting of a 2'-O-methyl modified nucleotide, a 2'-fluoro modified nucleotide, a nucleotide comprising a 5'-phosphorothioate group, a terminal nucleotide linked to a cholesterol derivative, a terminal nucleotide linked to a hydrophobic molecule, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base containing nucleotide.

9. The translation modulating agent of claim 1, wherein the ASO is between about 5 to about 100 nucleotides in length.

10. The translation modulating agent of claim 1, wherein the ASO is between about 10 to about 50 nucleotides in length.

11. The translation modulating agent of claim 1, wherein the expanded repeat protein region is selected from the group consisting of poly(GA), poly(GR), poly(GP), poly (PA) and poly(PR).

12. The translation modulating agent of claim 1, wherein the expanded repeat protein region is poly(GA).

* * * * *